United States Patent
Kandel et al.

(10) Patent No.: US 10,195,044 B2
(45) Date of Patent: Feb. 5, 2019

(54) INTERVERTEBRAL DISC IMPLANT

(71) Applicant: Sinai Health System, Toronto (CA)

(72) Inventors: Rita Kandel, Toronto (CA); J. Paul Santerre, Whitby (CA); Shu Qiu Li, Toronto (CA)

(73) Assignee: Sinai Health System, Toronto, Ontario (CA)

( * ) Notice: Subject to any disclaimer, the term of this patent is extended or adjusted under 35 U.S.C. 154(b) by 362 days.

(21) Appl. No.: 14/903,622

(22) PCT Filed: Jul. 11, 2014

(86) PCT No.: PCT/CA2014/000564
§ 371 (c)(1),
(2) Date: Jan. 8, 2016

(87) PCT Pub. No.: WO2015/003251
PCT Pub. Date: Jan. 15, 2015

(65) Prior Publication Data
US 2016/0143745 A1 May 26, 2016

Related U.S. Application Data

(60) Provisional application No. 61/845,679, filed on Jul. 12, 2013.

(51) Int. Cl.
*A61F 2/44* (2006.01)
*C12N 5/00* (2006.01)
(Continued)

(52) U.S. Cl.
CPC .............. *A61F 2/442* (2013.01); *A61L 27/12* (2013.01); *A61L 27/18* (2013.01);
(Continued)

(58) Field of Classification Search
CPC . A61F 2/44; A61F 2/442; A61L 27/38; A61L 27/3817; A61L 27/12; A61L 27/18; A61L 27/3895
See application file for complete search history.

(56) References Cited

U.S. PATENT DOCUMENTS

| 5,326,357 A | 7/1994 | Kandel |
| 6,077,989 A | 6/2000 | Kandel et al. |
| (Continued) | | |

FOREIGN PATENT DOCUMENTS

| CA | 2413353 | 1/2002 |
| CA | 2678422 | 8/2008 |

OTHER PUBLICATIONS

Seguin, C.A. et al., Tissue Engineered Nucleus Pulposus Tissue Formed on a Porous Calcium Polyphosphate Substrate, Spine, Jun. 2004, 29(12): 1299-1306.
(Continued)

*Primary Examiner* — Christopher Beccia
(74) *Attorney, Agent, or Firm* — Howson & Howson LLP

(57) ABSTRACT

The disclosure relates to an intervertebral disc implant comprising a first construct comprising a continuous layer of nucleus pulposus (NP) tissue directly or indirectly on and integrated with a substrate, and a second construct surrounding the first construct comprising one or more continuous layers of annulus fibrosus (AF) tissue on and adherent to a scaffold, wherein the AF tissue, which is composed of single or multiple adherent layers, is integrated with the NP tissue. The disclosure also relates to methods of preparing the multi-tissue intervertebral disc and using the intervertebral disc as an implant.

14 Claims, 20 Drawing Sheets

(51) Int. Cl.
| | |
|---|---|
| *A61L 27/18* | (2006.01) |
| *A61L 27/36* | (2006.01) |
| *A61L 27/38* | (2006.01) |
| *A61L 27/12* | (2006.01) |

(52) U.S. Cl.
CPC ....... *A61L 27/3608* (2013.01); *A61L 27/3612* (2013.01); *A61L 27/3817* (2013.01); *A61L 27/3856* (2013.01); *A61L 27/3895* (2013.01); *C12N 5/0068* (2013.01); *A61F 2002/4435* (2013.01); *A61F 2002/4445* (2013.01); *A61F 2002/4495* (2013.01); *A61L 2430/38* (2013.01)

(56) References Cited

U.S. PATENT DOCUMENTS

| | | | |
|---|---|---|---|
| 6,464,729 B1 * | 10/2002 | Kandel | A61L 27/3612 435/372 |
| 7,494,614 B2 | 2/2009 | Pilliar et al. | |
| 8,163,554 B2 | 4/2012 | Kandel | |
| 2011/0098826 A1 | 4/2011 | Mauck et al. | |
| 2013/0079881 A1 * | 3/2013 | Bonassar | A61K 35/32 623/17.16 |

OTHER PUBLICATIONS

Yang, L. et al., Polar Surface Chemistry of Nanofibrous Polyurethane Scaffold Affects Annulus Fibrosus Cell Attachment and Early Matrix Accumulation, Journal of Biomedical Materials Research. Part A, Dec. 2009, 91(4): 1089-1099.
International Search Report dated Oct. 16, 2014 in corresponding International Patent Application No. PCT/CA2014/000564, filed Jul. 11, 2014.
Written Opinion dated Oct. 16, 2014 in corresponding International Patent Application No. PCT/CA2014/000564, filed Jul. 11, 2014.
Ahmed N, et al. Cartilage Tissue Formation Using Re-differentiated Passaged Engineering In Vivo. Tissue Engineering Part A. 15(3):665-73, online publn Sep. 2008.
Ahmed, N.et al., Mesenchymal stem and progenitor cells for cartilage repair. Skeletal Radiol. 36:909-12, Nov. 2007.
Alini M, et al. The potential and limitations of a cell-seeded collagen/hyaluronan scaffold to engineer an intervertebral disc-like matrix. Spine 28(5): 446-54, Mar. 2003.
Allan K, et al. Formation of Biphasic Constructs Containing Cartilage with a Calcified Zone Interface. Tissue Engineering. 13(1):167-77, Feb 2007.
Baer, A.E.et al., Collagen gene expression and mechanical properties of intervertebral disc cell-alginate cultures. J Orthop Res. 19:2-10, Jan. 2001.
Bass, E.C.et al., Biaxial testing of human annulus fibrosus and its implications for a constitutive formulation. Ann Biomed Eng. 32:1231-42, Sep. 2004.
Beckstein, J.C. et al., Comparison of animal discs used in disc research to human lumbar disc: axial compression mechanics and glycosaminoglycan content. Spine (Phila Pa 1976). 33(6): E166-73, Mar. 2008.
Bowles, R.D.et al., Self-Assembly of Aligned Tissue-Engineered Annulus Fibrosus and Intervertebral Disc Composite Via Collagen Gel Contraction. Tissue Eng Part A. Apr.; 16(4): 1339-1348, Apr. 2010. Epub Jan. 2010.
Chang G, et al. Enhancing Annulus Fibrosus Tissue Formation in Porous Silk Scaffolds. J Biomed Mater Res A. 92(1):43-51, pub online Jan. 2009.
Chang G, et al., Porous Silk Scaffolds can be used for Tissue Engineering Annulus Fibrosus. Eur Spine J. 16(11):1848-57, Apr. 2007.
Chou, A.I. et al. The effect of serial monolayer passaging on the collagen expression profile of outer and inner anulus fibrosus cells. Spine (Phila Pa 1976). 31:1875-81, Aug. 2006.

Chou, A.I. et al. Distinct intervertebral disc cell populations adopt similar pheno-types in three-dimensional culture. Tissue Eng Part A 14:2079-2087, Dec. 2008.
Ebara, S. et al, Spine., Tensile properties of nondegenerate human lumbar anulus fibrosus. Spine (Phila Pa 1976);21(4):452-61, Feb. 1996.
Fang Z, et al, Differentiation of GFP-Bcl-2-engineered mesenchymal stem cells towards a nucleus pulposus-like phenotype under hypoxia in vitro. Biochem Biophys Res Commun.;432(3):444-50, Mar. 15, 2013.
Gan L, et al. Low-power Laser Stimulation of Tissue Engineered Cartilage Tissue Formed on a Porous Calcium Polyphosphate Scaffold. Lasers Surg Med. 39(3):286-293, Mar. 2007.
Gan L, Kandel R. In Vitro Cartilage Tissue Formation by Co-culture of Primary and Passaged Chondrocytes. Tissue Engineering. 13(4):831-42, Apr. 2007.
Ganey, T.et al., Intervertebral disc repair using adipose tissue-derived stem and regenerative cells: experiments in a canine model. Spine (Phila Pa 1976). 34:2297-304, Oct. 2009.
Gruber, H.E. et al., Autologous intervertebral disc cell implantation: a model using Psammomys obesus, the sand rat. Spine (Phila Pa 1976). 27:1626-33, Aug. 2002.
Grynpas, M.D.et al., Porous calcium polyphosphate scaffolds for bone substitute applications in vivo studies. Biomaterials. 23:2063-70, May 2002.
Hamilton DJ, et al. Formation of a nucleus pulposus-cartilage endplate construct in vitro. Biomaterials. 27:397-405, 2006. Publ online Sep. 2005.
Hamilton DJ, et al., Effect of circumferential constraint on nucleus pulposus tissue in vitro. Spine J. 10:174-83, Feb. 2010. Publ online Dec. 2009.
Helen W, et al., Three-dimensional culture of annulus fibrosus cells within PDLLA/Bioglass® composite foam scaffolds: Assessment of cell attachment, proliferation and extrcellular matrix production. Biomaterials 28(11): 2010-2020, 2007. Publ online Jan. 2007.
Hohaus, C. et al., Cell transplantation in lumbar spine disc degeneration disease. Eur Spine J. 17 Suppl 4:492-503, 2008. Publ online Nov. 2008.
Ishihara, H. and Urban, J. P. Effects of low oxygen concentrations and metabolic inhibitors on proteoglycan and protein synthesis rates in the intervertebral disc. J.Orthop.Res. 17:829-835, Nov. 1999.
Jin, L. et al, The challenge and advancement of annulus fibrosus tissue engineering. Eur Spine J., 22:1090-1100, Jan. 2013.
Johnson, W. E., et al., Topographical guidance of intervertebral disc cell growth in vitro: towards the development of tissue repair strategies for the anulus fibrosus. Eur. Spine J. 15:S389-S396, 2006. Publ online May 2006.
Jukes, J.M. et al., Critical Steps toward a tissue-engineered cartilage implant using embryonic stem cells. Tissue Eng Part A. 14:135-47, Jan. 2008.
Kandel RA, et al., Repair of Osteochondral Defects with Biphasic Cartilage-Calcium Polyphosphate Constructs in a Sheep Model. Biomaterials 27(22):4120-31, Mar. 2006.
Kandel, R. et al., Characterization of the mineral in calcified articular cartilagenous tissue formed in vitro. Tissue Eng. 5(1):25-34, Feb. 1999.
Kandel, R.A. et al., In vitro formation of mineralized cartilagenous tissue by articular chondrocytes. In Vitro Cell Dev Biol Anim. 33:174-81, Mar. 1997.
Kandel, RA. et al, Tissue engineering and the intervertebral disc: the challenges. Eur Spine J, 17 Suppl 4: S480-S491, Dec. 2008. Publ online Nov. 2008.
Khan AA, et al. The effect of continuous culture growth and structure of tissue-engineered cartilage. Biotechnol Prog. 25(2):508-15, Mar. 2009.
Le Visage C, et al. Interaction of Human Mesenchymal Stem Cells With Disc Cells: Changes in Extracellular Matrix Biosynthesis. Spine. 31:2036-2042, Aug. 2006.
Maherali et al, A high efficiency system for the generation and study of human induced pluripotent stem cells; Cell Stem Cell 3:340-5, Sep. 2008.

(56) References Cited

OTHER PUBLICATIONS

Mauck et al, Regional multilineage differentiation potential of meniscal fibro-chondrocytes: implications for meniscus repair. Anat Rec (Hoboken); 290(1):48-58, Jan. 2007.

Mauck, R.L.et al., Chondrogenic differentiation and functional maturation of bovine mesenchymal stem cells in long-term agarose culture. Osteoarthritis Cartilage. 14:179-89, Feb. 2006.

Mauck, R.L.et al., Regulation of cartilaginous ECM gene transcription by chondrocytes and MSCs in 3D culture in response to dynamic loading. Biomech Model Mechanobiol. 6:113-25, Jan. 2007.

Meinel L, et al., Engineering cartilage-like tissue using human mesenchymal stem cells and silk protein scaffolds. Biotechnol Bioeng.;88(3):379-91, Nov. 2004. Publ online Oct. 2004

Meisel, H.J.et al., Clinical experience in cell-based therapeutics: disc chondrocyte transplantation A treatment for degenerated or damaged intervertebral disc. Biomol Eng. 24:5-21, Feb. 2007. Publ online Jul. 2006.

Mizuno H, et al. Tissue-engineered composites of annulus fibrosus and nucleus pulposus for intervertebral disc replacement. Spine 29: 1290-1298, discussion 1297-8, Jun. 2004.

Mizuno, H.et al., Biomechanical and biochemical characterization of composite tissue engineered intervertebral discs. Biomaterials. 27(3):362-70, Jan. 2006. Publ online Sep. 2005.

Muller et al, Induced pluripotent stem cells as a tool for gaining new insights into Fanconi anemia; Mol Ther. 17:947-53, Aug. 2009; Publ online Jul. 2012.

Nerurkar NL, et al. Mechanics of oriented electrospun nanofibrous scaffolds for annulus fibrosus tissue engineering. J Orthop Res. 25:1018-28, Aug. 2007.

Nerurkar, N.L.et al., Mechanical design criteria for intervertebral disc tissue engineering. J Biomech. 43(6): 1017-1030, Apr. 2010, publ online Jan. 2010.

Nerurkar, NL, et al., Nanofibrous biologic laminates replicate the form and function of the annulus fibrosus. Nat Mater. 8:986-92, Dec. 2009, publ online Oct. 2009.

Nesti, L.J.et al., Intervertebral disc tissue engineering using a novel hyaluronic acid anofibrous scaffold (HANFS) amalgam. Tissue Eng Part A. 14:1527-37, Sep. 2008.

Nomura, T. et al., Nucleus pulposus allograft retards intervertebral disc degeneration. Clin Orthop Relat Res.94-101, Aug. 2001.

O'Halloran, D. M. and Pandit, A. S. Tissue-engineering approach to regenerating the intervertebral disc. Tissue Eng 13:1927-1954, Aug. 2007.

Okuma, M.et al., Reinsertion of stimulated nucleus pulposus cells retards intervertebral disc degeneration: an in vitro and in vivo experimental study. J Orthop Res. 18:988-97, Nov. 2000.

Pilliar, R.M.et al., Porous calcium polyphosphate scaffolds for bone substitute applications—in vitro characterization. Biomaterials. 22(9):963-72, May 2001.

Richardson et al, Intervertebral disc cell-mediated mesenchymal stem cell differentiation. Stem Cells. Mar;24(3):707-16, Sep. 2006.

Richardson, S.M., et al., Intervertebral disc biology, degeneration and novel tissue engineering and regenerative medicine therapies. Histol Histopathol, 22(9):1033-41, Sep. 2007.

Rong Y, et al. Proteoglycans synthesized by canine intervertebral disc cells grown in a type I collagen-glycosaminoglycan matrix. Tissue Eng 8:1037-47, Dec. 2002.

Roughley, P.et al., The potential of chitosan-based gels containing intervertebral disc cells for nucleus pulposus supplementation. Biomaterials. 27:388-96, Jan. 2006. Publ online Aug. 2005.

Ruan, D.et al., Intervertebral disc transplantation in the treatment of degenerative spine disease: a preliminary study. Lancet. 369:993-9, Mar. 2007.

Santerre, J.P, et al. Understanding the biodegradation of polyurethanes: from classical implants to tissue engineering materials. Biomaterials 26(35):7457-70, Dec. 2005.

Satija, et al, Mesenchymal stem cell-based therapy: a new paradigm in regenerative medicine; J Cell Mol Med, Nov.-Dec.; 13(11-12): 4385-4402, Nov. 2009; publ online Jul. 2009.

Sato, M. et al. An atelocollagen honeycomb-shaped scaffold with a membrane seal ACHMS scaffold) for the culture of annulus fibrosus cells from an intervertebral disc. J. Biomed. Mater. Res. A 64:248-256, Feb. 2003.

Schumann, D.et al., Mechanobiological conditioning of stem cells for cartilage tissue engineering. Biomed Mater Eng. 16:S37-52, Feb. 2006.

Sha'Ban, M.et al., Fibrin promotes proliferation and matrix production of intervertebral disc cells cultured in three-dimensional poly(lactic-co-glycolic acid) scaffold. J Biomater Sci Polym Ed. 19:1219-37, Sep. 2008.

Shanjani Y, et al. Solid freeform fabrication and characterization of porous calcium polyphosphate structures for tissue engineering purposes. J Biomed Mater Res B Appl. Biomater. 93(2):510-9, May 2010; publ online Feb. 2010.

Shanjani Y, et al. Solid freeform fabrication of porous calcium polyphosphate structures for bone substitute applications: in vivo studies. J Biomed Mater Res B Appl Biomater. 101(6):972-80, Aug. 2013; publ online Mar. 2013.

Shao X, Hunter CJ. Developing an alginate/chitosan hybrid fiber scaffold for annulus fibrosus cells. J Biomed Mater Res A 82(3):701-10, Sep. 2007; publ online Feb. 2007.

Spiteri, C.G., et al., Substrate porosity enhances chondrocyte attachment, spreading, and cartilage tissue formation in vitro. J Biomed Mater Res A,78(4): p. 676-83, Sep. 2006; publ online May 2006.

Strassburg et al, Co-culture induces mesenchymal stem cell differentiation and modulation of the degenerate human nucleus pulposus cell phenotype. Regen Med. 5(5):701-11, Sep. 2010.

Takahashi et al, Induction of pluripotent stem cells from mouse embryonic and adult fibroblast cultures by defined factors; Cell 126: 663-76, Aug. 2006.

Taylor D, et al. Proteoglycan and collagen accumulation by passaged chondrocytes can be enhanced through side by side culture with primary chondrocytes. Tissue Eng Part A. 16(2); 643-651, Feb. 2010.

Thonar E, et al. Compartmentalization of the matrix formed by nucleus pulposus and annulus fibrosus cells in alginate gel. Biochem Soc Trans 30(Pt 6): 874-8, Nov. 2002.

Toh WS et al, Differentiation and enrichment of expandable chondrogenic cells from human embryonic stem cells in vitro. J Cell Mol Med, 13(9B):3570-90, Sep. 2009.

Vadalà G, et al, Coculture of Bone Marrow Mesenchymal Stem Cells and Nucleus Pulposus Cells Modulate Gene Expression Profile Without Cell Fusion., Spine (Phila Pa 1976). 33(8):870-6, Apr. 2008.

Waldman SD, et al. Characterization of cartilaginous tissue formed on calcium polyphosphate substrates in vitro. J Biomed Mater Res 62(3): 323-330, Dec. 2002.

Waldman SD, et al. Multi-axial Mechanical Stimulation of Tissue Engineered Cartilage. Eur Cell Mater. 13:66-75, Apr. 2007.

Wan, Y.et al., Biphasic scaffold for annulus fibrosus tissue regeneration. Biomaterials. 29: 643-52, Feb. 2008. Publ online Nov 2007.

Wilda, H. and Gough, J. E. In vitro studies of annulus fibrosus disc cell attachment, differentiation and matrix production on PDLLA/45S5 Bioglass composite films. Biomaterials 27(30):5220-5229, Oct. 2006; publ online Jun. 2006.

Woltjen et al, piggyBac transposition reprograms fibroblasts to induced pluripotent stem cells. Nature 458: 766-70, Apr. 2009; Publ online Mar. 2009.

Wu et al., Generation of Pig Induced Pluripotent Stem Cells with a Drug-Inducible System; J Mol Cell Biol 1:46-54, Oct. 2009; Publ online Jun. 2009.

Yang SH, et al. An in-vitro study on regeneration of human nucleus pulposus by using gelatin/chondroitin-6-sulfate/hyaluronan tricopolymer scaffold. Artif Organs. 29: 806-14, Oct. 2005.

Yang SH, et al. Gelatin/chondroitin-6-sulfate copolymer scaffold for culturing human nucleus pulposus cells in vitro with production of extracellular matrix. J Biomed Mater Res B Appl Biomater. 74: 488-94, Jul. 2005.

Yang, X. and X. Li, Nucleus pulposus tissue engineering: a brief review. Eur Spine J 18: 1564-1572, Nov. 2009; publ online Jul. 2009.

(56) References Cited

OTHER PUBLICATIONS

Yuan et al, Effects of nucleus pulposus cell-derived acellular matrix on the differentiation of mesenchymal stem cells. Biomaterials. 34(16):3948-61, May 2013. Publ online Mar. 2013.

Zhu H, et al. The role of the hyaluronan receptor CD44 in mesenchymal stem cell migration in the extracellular matrix. Stem Cells. 24:928-35, Apr. 2006. Publ online Nov. 2005.

* cited by examiner

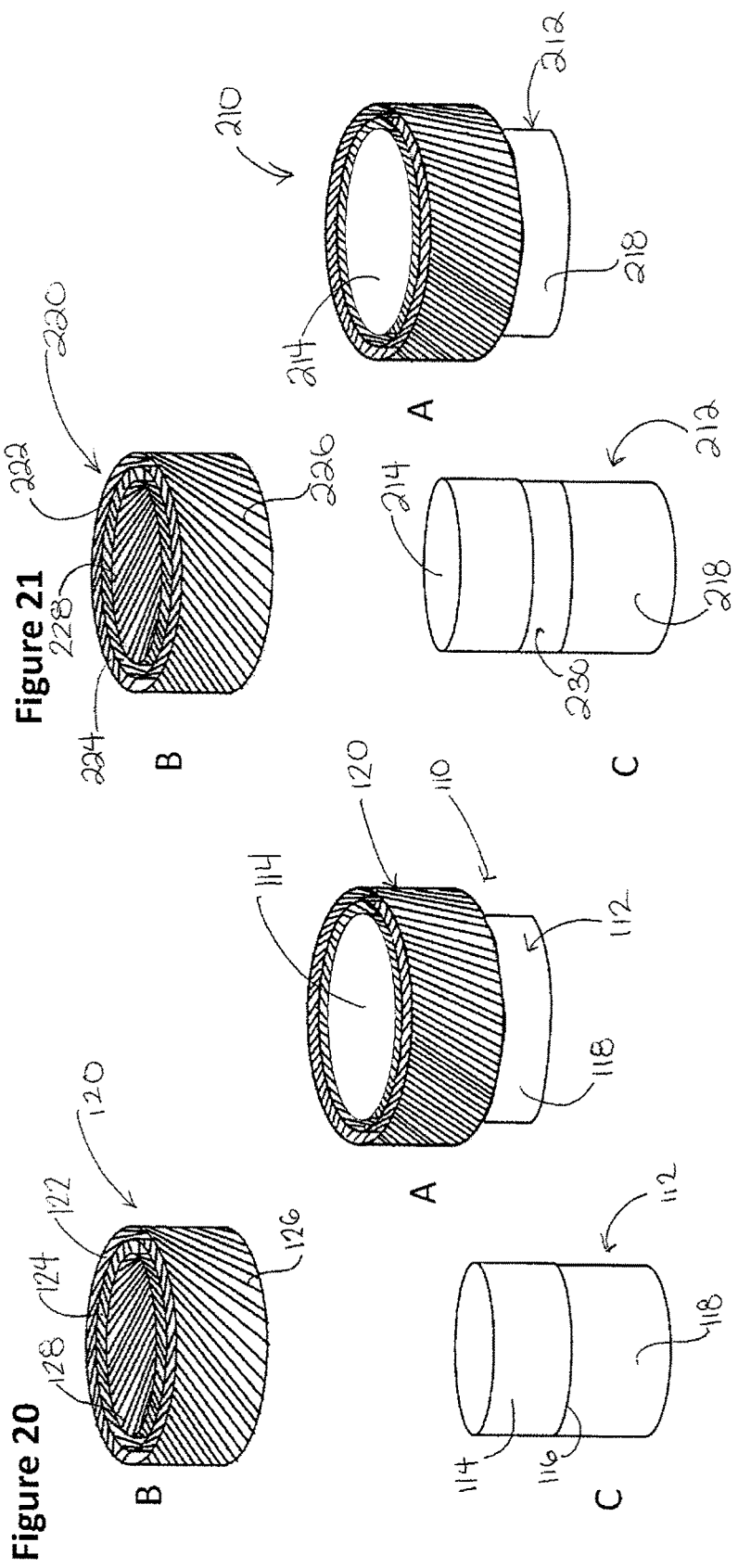

INTERVERTEBRAL DISC IMPLANT

CROSS-REFERENCE TO RELATED APPLICATIONS

This application is a national stage of International Patent Application No. PCT/CA2014/000564, filed Jul. 11, 2014, which claims the benefit of the priority of U.S. Provisional Patent Application No. 61/845,679, filed Jul. 12, 2013, which applications are incorporated herein by reference.

FIELD

The disclosure relates to an integrated intervertebral disc implant and methods and uses thereof for replacing a damaged or deficient natural intervertebral disc. The disclosure also relates to methods of preparing and using the intervertebral disc implant.

BACKGROUND

The intervertebral disc (IVD) is a symphysis-type joint and is a specialized structure consisting of interdependent tissues, the annulus fibrosus (AF), the nucleus pulposus (NP) which are sandwiched between two cartilage endplates (CEP) that are integrated to the adjacent vertebral bodies (VBs) (FIG. 1). The AF is an angle ply tissue which surrounds the NP and both tissues are integrated to the CEP which is integrated to the VBs. Degradation of the disc is similar to that which occurs in osteoarthritis, resulting in pain and limited mobility. Degenerative intervertebral disc disease is very common and the neck/back pain that can develop as a result of this disease has a lifetime prevalence of 80%. Approximately 1 in 50 Canadians become disabled by back pain and 40% of all workplace absences in Canada are due to back pain. The annual cost in terms of lost productivity, medical expenses and workers' compensation benefits was calculated to be at least $100 billion in 2002 in the United States alone. There is a growing consensus that currently used surgical treatments are not effective and cannot be further optimized. Thus, there is an interest in developing cell based therapies to yield regenerated tissues to treat the chronic pain that arises from disc degeneration.

SUMMARY

The present inventors have generated the tissues that comprise the intervertebral disc and have established viable protocols and tissue conditions that facilitate integration of all the tissue components into one functional tissue so it can weight bear following implantation. In particular, the inventors have prepared an intervertebral disc implant containing different integrated components (the annulus fibrosus (AF) wherein the AF is comprised of multiple layers of tissue each layer having fibres that are oriented at oblique angles to fibres of the adjacent layer, the nucleus pulposus (NP) and, optionally, at least one cartilaginous layer or end plate).

Accordingly, the disclosure relates to an integrated intervertebral disc implant that has tissue which structurally approaches that of a natural intervertebral disc and can be used as a replacement for a damaged, degenerated or deficient disc.

In an aspect, the disclosure provides an intervertebral disc implant comprising (a) a first construct comprising a continuous layer of nucleus pulposus (NP) tissue directly or indirectly on and integrated with a first substrate, and (b) a second construct surrounding the first construct comprising one or more continuous layers of annulus fibrosus (AF) tissue on and adherent to a second substrate, wherein the AF tissue is integrated with the NP tissue. In an aspect, the AF and NP tissues are integrated to provide an engineered intervertebral disc that mimics a native intervertebral disc or anatomically shaped intervertebral disc for use for example, for disc replacement. The second substrate is also referred to herein as a scaffold and in such instance, the first substrate is referred to as the substrate.

Accordingly, in an aspect, the disclosure provides an intervertebral disc implant comprising (a) a first construct comprising a continuous layer of nucleus pulposus (NP) tissue directly or indirectly on and integrated with a substrate, and (b) a second construct surrounding the first construct comprising one or more continuous layers of annulus fibrosus (AF) tissue on and adherent to a scaffold, wherein the AF tissue is integrated with the NP tissue. In an aspect, the AF and NP tissues are integrated to provide an engineered intervertebral disc that mimics a native intervertebral disc or anatomically shaped intervertebral disc for use for disc replacement.

The substrate may be bone or an engineered biomaterial, in particular a bone substitute. The scaffold may be a polymeric substrate, such as a synthetic elastomeric polymeric substrate. In an aspect, the scaffold is a silk scaffold. In another aspect, the scaffold comprises polyurethane fibres, more particularly polycarbonate urethane (PU) fibres. The scaffold may optionally comprise additives that enhance cell and/or protein interactions with the substrate. In one embodiment, the scaffold comprises low molecular weight polymer additives containing hydroxyl/carboxylic acid groups that enhance cell and/or protein interactions with the scaffold. In one embodiment, the scaffold is non-ester containing polyurethane elastomers containing anionic/dihydroxyl oligomeric (ADO) additives.

In an aspect, the disclosure provides an intervertebral disc implant comprising (a) a first construct comprising a continuous layer of nucleus pulposus (NP) tissue on and integrated with a substrate, and (b) a second construct surrounding the first construct comprising one or more continuous layers of annulus fibrosus (AF) tissue on and adherent to a scaffold, wherein the AF tissue is integrated with the NP tissue and the substrate is bone or an engineered biomaterial and the scaffold is a polymeric substrate.

In an aspect, the AF tissue of the implant is characterized by one or more of the following:
1. actin cytoskeleton oriented parallel to the long axis of the cell mimicking the actin organization in AF cells during tissue development and in fully formed tissue.
2. Type I collagen, the major matrix molecule of AF tissue, is present throughout tissue
3. Type I collagen initially, is oriented parallel to the cell and fibrillar fibronectin (also present in the developing AF).
4. collagen fibres extending out of the cell in a polarized manner similar to human AF cells in vivo;
5. where more than one layer of AF/scaffold, the layers of AF tissue/scaffold are adherent to each other.

In a particular aspect, the continuous layer of nucleus pulposus (NP) tissue is directly or indirectly on and integrated with the subsurface of the substrate and the substrate protrudes from the NP and AF tissue. Thus, the disclosure provides a tissue-engineered intervertebral disc comprising (a) a first construct comprising a substrate comprising a continuous layer of nucleus pulposus (NP) tissue on and integrated with the subsurface of the substrate, and (b) a second construct surrounding the NP tissue of the first construct and comprising one or more continuous layers of annulus fibrosus (AF) tissue on and adherent to a scaffold, wherein the AF tissue is integrated with the NP tissue.

In an embodiment, the part of the implant comprising the continuous layer of NP tissue surrounded by layers of AF tissue is on one end of the substrate and the continuous layer of NP tissue is integrated with the subsurface of the substrate.

The intervertebral implant may be configured to be implanted within an intervertebral space between adjacent vertebra bodies. In an aspect, the implant may be configured so that it has a first exterior interfacing surface engaging a first (proximal) vertebra and a second exterior interfacing surface (distal) engaging a second vertebra. The first exterior interfacing surface may comprise the AF tissue and NP tissue of the implant and the second exterior interfacing surface may comprise the exterior surface of the substrate.

In an aspect, two implants turned inwards may be implanted wherein the components of the implants comprising the NP tissue and AF tissue are adjacent and the substrate components of the implants interface with the adjacent vertebra body.

In a further aspect, an intervertebral implant and a first construct (e.g. NP and substrate) can be implanted within an intervertebral space between adjacent vertebra bodies, wherein the NP tissue and AF tissue of the intervertebral disc (IVD) and the NP of the first construct are adjacent and the substrate components of the implant and the first construct interface with the respective adjacent vertebra body.

In yet another aspect, an intervertebral implant and a cartilaginous layer on a substrate are implanted within an intervertebral space between adjacent vertebra bodies, wherein the NP tissue and AF tissue of the IVD and the cartilage tissue of the first construct are adjacent and the substrate components of the implant and the substrate component of the cartilaginous layer/substrate interface with the respective adjacent vertebra body.

The implant may additionally comprise cartilaginous tissue adjacent to the component of the implant comprising the NP and AF tissues.

In an aspect, the first construct of the implant may additionally comprise cartilaginous tissue or a cartilage endplate between the NP and substrate, wherein the NP tissue is on and adherent to the cartilaginous tissue. Therefore, the disclosure provides an intervertebral disc implant wherein the first construct comprises a continuous layer of regenerated or tissue-engineered NP tissue adherent to cartilaginous tissue on and integrated with the substrate. In such an embodiment, the first construct is a triphasic construct comprising a continuous layer of NP tissue adherent to cartilaginous tissue integrated with the substrate, such as a bone substitute. In such embodiments, the NP tissue would be considered indirectly on and integrated with the substrate. In an embodiment, the continuous layer of cartilage tissue may comprise an engineered calcified cartilage tissue or a bizonal cartilage tissue comprising a continuous layer of cartilage tissue engineered on the substrate interfaced via a zone of calcified cartilage tissue.

In an embodiment, the second construct may comprise two or more, three or more, four or more, five or more, or ten or more layers, optionally five or more layers, each layer comprising regenerated or engineered AF tissue formed on the scaffold, resulting in a multi-lamellate AF tissue. In an embodiment, the fibres in each layer are at an oblique angle to the fibres of the adjacent layer and the layers are adherent to each other.

In an embodiment, the multi-lamellate AF tissue is characterized by one or more of the following properties:
1. actin cytoskeleton oriented parallel to the long axis of the cell mimicking the actin organization in AF cells during tissue development and in fully formed tissue.
2. Type I collagen, the major matrix molecule of AF tissue, is present throughout tissue
3. Type I collagen initially, is oriented parallel to the cell and fibrillar fibronectin (also present in the developing AF).
4. collagen fibres extending out of the cell in a polarized manner similar to human AF cells in vivo;
5. layers of AF tissue/scaffold are adherent to each other.

In an embodiment, an intervertebral disc implant comprises nucleus pulposus tissue integrated with and into the subsurface of a porous bone substitute surrounded by annulus fibrosus cell-seeded polyurethane nanofibrous scaffold aligned integrated multi-lamellated tissue wherein each lamellae is at an oblique angle to each other.

The disclosure also provides a method for preparing an intervertebral disc implant comprising (a) preparing a first construct by culturing NP cells or precursors thereof on a substrate to form a continuous layer of NP tissue directly or indirectly on and integrated with the substrate; (b) preparing a second construct by culturing AF cells or precursors thereof on a scaffold to form one or more continuous layers of AF tissue on and adherent to the scaffold; wherein the layers are adherent to each other to form a single tissue; (c) combining the first construct and second construct so that the second construct surrounds the first construct and the NP tissue and AF tissue are adjacent; and (d) culturing the combined first construct and second construct so they become integrated and form the intervertebral disc implant. In a particular aspect, the substrate comprises the continuous layer of nucleus pulposus (NP) tissue is fabricated on and integrated with the subsurface of the substrate and the first and second constructs are combined such that the second construct surrounds the first construct so that the continuous layers of annulus fibrosus (AF) tissues are adjacent to and integrated with the NP tissue.

The method to prepare the implant may additionally comprise culturing cartilage tissue on the substrate of the first construct prior to the addition of NP tissue. Thus, the method for preparing the implant can further comprise culturing cartilage tissue on the substrate prior to step (a) to form a continuous layer of cartilage tissue on and integrated with the substrate so that in step (a) the continuous layer of NP tissue forms on and is adherent to cartilage tissue on the substrate, i.e. the NP tissue indirectly forms on and is integrated with the substrate. The continuous layer of cartilage tissue may comprise an engineered calcified cartilage tissue or a bizonal cartilage tissue comprising a continuous layer of cartilage tissue engineered on the substrate interfaced via a zone of calcified cartilage tissue.

The disclosure also provides a method for producing an engineered calcified cartilage tissue comprising: a) seeding isolated or differentiated chondrocytes or chondrocytes obtained from precursor cells grown under chondro-inducing conditions on the substrate, such as bone or engineered biomaterial substrate; b) culturing the chondrocytes in the presence of a mineralizing agent under suitable conditions to generate a calcified cartilage tissue on the substrate characterized by accumulation of collagen type X, OH-apatite mineral, collagen type II and proteoglycans. The method may further comprise culturing isolated chondrocytes on the engineered calcified cartilage tissue to generate a bizonal cartilage tissue comprising a continuous layer of cartilage tissue engineered on the substrate interfaced via a zone of calcified cartilage tissue.

Accordingly, a method is provided for preparing an integrated intervertebral disc implant comprising a) preparing a first construct by (i) seeding isolated chondrocytes or chondrocytes obtained from precursor cells grown under chondro-inducing conditions on a substrate; (ii) culturing the chondrocytes in the presence of a mineralizing agent under suitable conditions to generate a calcified cartilage tissue on the substrate characterized by accumulation of collagen type X, mineral, collagen type II and proteoglycans; and (iii) culturing NP cells or precursors on the cartilage/substrate produced in (ii) to form a continuous layer of NP tissue on and adherent to the cartilaginous layer which is on and integrated with the substrate; b) preparing a second construct by culturing AF cells or precursors thereof on a scaffold to form two or more continuous layers of AF tissue-scaffold, wherein the layers are adherent to each other to form a single tissue; c) combining the first construct and second construct so that the second construct surrounds the first construct and the NP tissue and AF tissue are adjacent; and d) culturing the combined first construct and second construct to prepare the integrated intervertebral disc implant. In an aspect, the method further comprises in a) culturing isolated chondrocytes on the engineered calcified cartilage tissue to generate a bizonal cartilage tissue comprising a continuous layer of cartilage tissue engineered on the substrate interfaced with a zone of calcified cartilage tissue after (ii) and before (iii).

In an aspect of the method for preparing the implant, step (b) further comprises culturing the second construct. The second construct may be cultured under suitable conditions prior to combining with the first construct in step (c). In an aspect, the second construct is cultured for about up to 1 week, in particular for 24 hours, 48 hours, 3 days, 4 days, 5 days or 6 days, up to 2, 3, 4, 5 or 6 weeks, 1 to 8 weeks, 2 to 6 weeks, 2 to 4 weeks, or 4 to 6 weeks in a bioreactor, in particular a spinner or flow bioreactor.

The scaffold or second construct may be formed into a shape configured so that in step (c) the second construct can surround the first construct and the NP tissue and AF tissue are adjacent. In an aspect the scaffold or second construct is formed into a disc-shape with a hole extending through the center, and the first construct is inserted in the hole. In an aspect the scaffold or second construct is formed into a donut-shape with a cylindrical hole extending through the center, and the first construct is inserted in the cylindrical hole.

In an aspect of the method, the AF tissue is comprised of alternating layers of the AF scaffold where in a first fibre scaffold layer is covered by AF tissue and then by a second scaffold layer containing tissue, wherein the fibres of the layer are at an oblique angle to the fibres of the first one, and to each other (said angle being between 20 and 70 degrees to each other). The dual layer scaffold and AF tissue is then wrapped around the NP/CPP construct described above, such as to form at least two wraps (i.e. two AF/scaffold dual layers) but optionally more than three wraps or layers of the dual layered AF scaffold.

The combined first construct and second construct may be grown in culture under suitable conditions. For example, the combination may be grown in a bioreactor for up to 1 week, in particular for 24 hours, 48 hours, 3 days, 4 days, 5 days or 6 days, or up to 2, 3, 4, 5 or 6 weeks, optionally up to 1 week. In an aspect, combined constructs are grown in a spinner bioreactor. This facilitates integration of the engineered tissues.

The disclosure provides methods of generating an intervertebral disc from at least two, optionally 3 separate tissues into an integrated composite that mimics the native intervertebral disc.

The disclosure provides methods of using the integrated intervertebral disc implant disclosed herein to replace or repair damaged or deficient intervertebral discs either as partial implants or full implants, and methods for repairing damaged or degenerated intervertebral discs. Methods disclosed herein may be used to treat vertebrates suffering from degenerated intervertebral disc conditions and in particular to treat humans with such conditions.

The disclosure also provides a method of replacing a damaged intervertebral disc and adjacent bone comprising replacing the damaged disc with an intervertebral disc implant disclosed herein. The disclosure also relates to an intervertebral disc implant disclosed herein for use in replacing a damaged disc and adjacent bone. The disclosure further relates to use of an intervertebral disc implant for replacing a damaged disc and adjacent bone.

The disclosure contemplates a method of replacing or repairing damaged or deficient intervertebral discs and adjacent bone of a patient comprising implanting one or more intervertebral disc implants disclosed herein into the site of the damaged or deficient intervertebral disc of the patient. Methods for enhancing healing of an intervertebral disc in a patient are contemplated which comprise inserting an intervertebral disc implant into the site of a damaged intervertebral disc.

In an aspect, the disclosure provides a method for replacing or repairing a degenerated or damaged intervertebral disc comprising implanting in the disc space, after the removal of the degenerated or damaged disc and adjacent bone an intervertebral disc implant disclosed herein.

Other objects, features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DESCRIPTION OF THE DRAWINGS

The disclosure will now be described in relation to the drawings in which:

FIG. 20A is a perspective view of an embodiment of an intervertebral disc implant. FIG. 20B is a perspective view of the second construct of the invertebral disc implant of FIG. 20A. FIG. 20C is a perspective view of the first construct of the invertebral disc implant of FIG. 20A.

FIG. 21A is a perspective view of another embodiment of an intervertebral disc implant. FIG. 21B is a perspective view of the second construct of the invertebral disc implant of FIG. 21A. FIG. 21C is a perspective view of the first construct of the invertebral disc implant of FIG. 21A.

DETAILED DESCRIPTION

Figure 1:
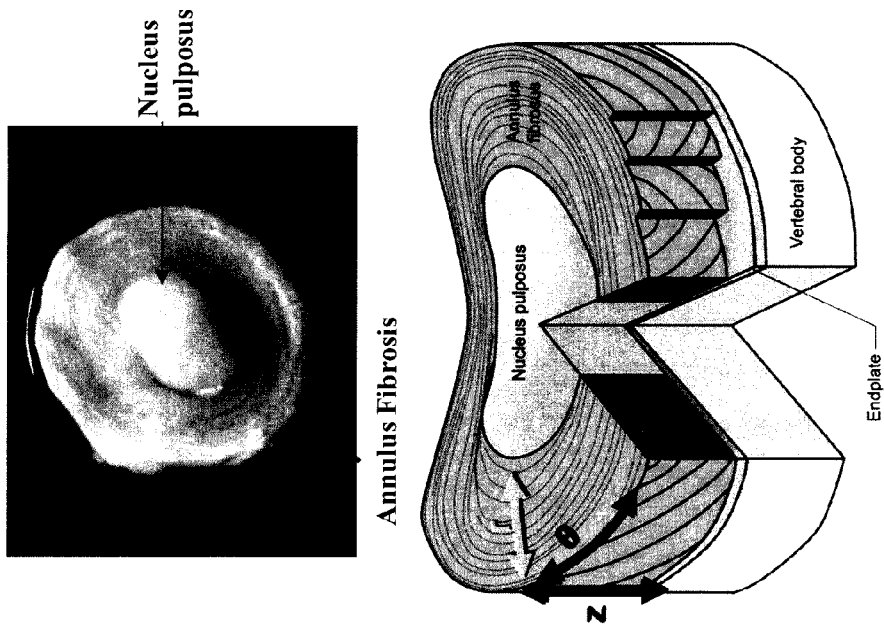
FIG. 1 shows an illustration of a native bovine disc, a photograph of a native bovine disc and a line diagram of the disc and adjacent vertebral body [*Kinesiology of the Musculoskeletal System, Foundations for Rehabilitation*, 2$^{nd}$ ed, Donald A. Neumann, 2010, Mosby Elsevier, ISBN 978-0-323-03989-5 and Nerurkar N et al. *J Biomech* 43:1018, 2010].
Figure 1:
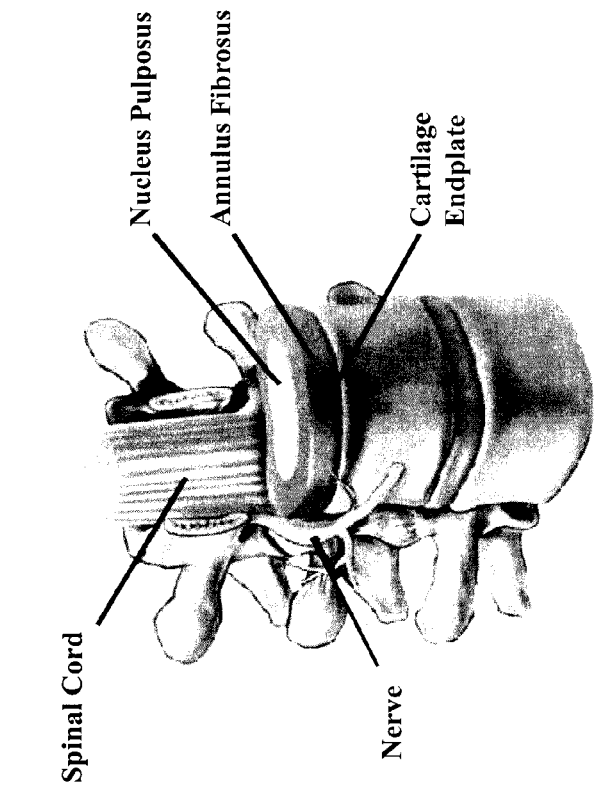
Figure 2:
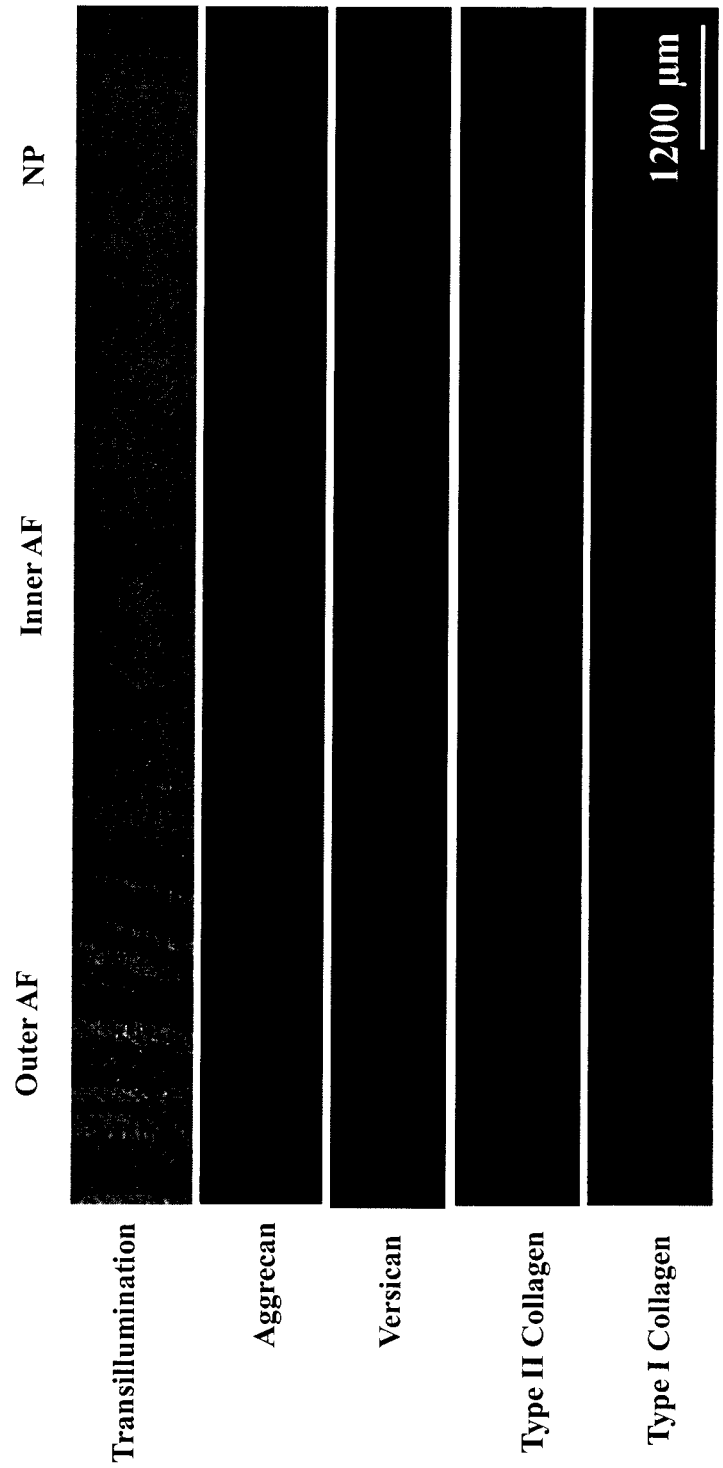
FIG. 2 shows a cross section of a histological image of the native bovine disc and immunostained for the major macromolecules present in the NP and AF tissue. A cross section of the native bovine IVD from nucleus pulposus (NP) to outer annulus fibrosus (AF) was examined histologically after immunostaining for proteoglycans, versican and aggrecan, and collagens, type I and II, using specific antibodies and fluorescent labelled secondary antibodies. Aggrecan and versican are present in the NP and inner AF. Versican is also present in the interlamellar space in the outer AF. Type I and II collagens are both present in the inner AF whereas type I collagen is only present in the outer AF. This differential composition is characteristic of the two zones, the inner and outer AF of the native AF.

Numerical ranges recited herein by endpoints include all numbers and fractions subsumed within that range (e.g., 1 to 5 includes 1, 1.5, 2, 2.75, 3, 3.90, 4, and 5). All fractions or integers between and including the two numbers are included in the range. It is also to be understood that all numbers and fractions thereof are presumed to be modified by the term "about." The term "about" means plus or minus 0.1 to 50%, 5-50%, or 10-40%, optionally 10-20%, and particularly 10% or 15%, of the number to which reference is being made. As used herein and in the appended claims, the singular forms "a", "an", and "the" include plural reference unless the context clearly dictates otherwise. As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The phrase "integrated with" or "adherent to" as used herein refers to two or more components coming together such that they remain together when handled. In relation to the integration of NP tissue with the substrate as disclosed herein, integrated also may mean that at least some of the NP cells enter the pores of the substrate and form tissue anchoring the tissue to the substrate. Adherent for example in relation to the AF scaffold means that cells attach to scaffold and then produce tissue such that the resulting tissue (i.e. extra-cellular matrix and cells) and scaffold are continuous and form a tissue that does not fall apart.

Second Construct

Primary, passaged or precursor AF cells may be used to prepare the regenerated AF tissues of the second construct. In an aspect, the AF tissue is prepared from primary AF cells. In another aspect, the AF tissue is prepared from AF precursor cells, including without limitation, mesenchymal stromal cells (MSC), embryonic stem cells (ES) and induced pluripotent stem cells (iPS).

Primary AF cells can be obtained from natural sources and they may be expanded in culture using conventional methods [See for example, Chou et al, Spine (Phila Pa. 1976), 31: 1875-81, 2006 and Baer et al, J Orthop Res. 19: 2-10, 2001]. AF cells (and NP cells for use in the first construct) may be isolated from intervertebral discs (lumbar discs, thoracic discs, or cervical discs) from animals, optionally humans, bovines, ovines, rabbits, particularly humans. The tissue may be isolated from adult or fetal tissue and can be isolated from outer AF, inner AF or combined inner and outer AF. In one aspect, the cells are isolated from intervertebral disc of the lumbar spine of an animal. Intervertebral disc tissue may be extracted from a patient being treated, or alternatively from a donor, using known surgical techniques. Cells may be isolated from intervertebral disc tissue by sequential enzyme digestion techniques, such as those described in Iu J. et al. Tissue Engineering, 2014. For example, the cells may be treated with 0.3% protease followed by 0.2% bacterial collagenase.

Mesenchymal stromal cells which have been isolated from different species, including without limitation humans and cows, may also serve as a source of AF cells [See for example, Ahmed et al, Skeletal Radiol. 36: 909-12, 2007; Satija, et al, J Cell Mol Med, 2009; and Mauck et al, Osteoarthritis Cartilage 14: 179-89, 2006]. MSCs include plastic-adherent multipotent cells that can differentiate into osteoblasts, chondroblasts and/or adipocytes under the appropriate conditions. MSCs can be readily obtained (e.g. aspirate) from many tissues including without limitation bone marrow (BM) and adipose tissue. MSCs may be expanded in monolayer culture without loss of phenotype [See, Satija et al, supra]. Embryonic stem cells, in particular human embryonic stem cells (hES), which have the ability to differentiate into MSCs, may be used as a source of AF cells [See for example, Toh et al, J Cell Mol Med 2009; Jukes et al, Tissue Eng Part A. 14: 135-47, 2008]. Another source of AF cells may be induced pluripotent stem cells (iPS), which may be derived from an individual's own somatic cells. iPS cells can be generated, as an example by transfection of the four transcription factors, Oct4, Sox2, c-Myc, and Klf4 (Yamanaka factors), into somatic cells, examples of which include mouse, pig, and human fibroblasts, beta cells, and B lymphocytes [See for example, Takahashi et al, Cell 126: 663-76, 2006; Maherali et al, Cell Stem Cell 3:340-5, 2008; and Wu et al., J Mol Cell Biol 1:46-54, 2009]. iPS cells can be generated in other ways. (eg. Zhou Y Y and Zeng F. Genomics Proteomics Bioinformatics. 2013 October; 11(5):284-7) iPS cells are in a pluripotent state and like ES cells proliferate and form colonies and teratomas [Muller et al, Mol Ther. 17:947-53, 2009 and Nishikawa et all, Nat Rev Mol Cell Biol 9: 725-9, 2008]. Viral-mediated protocols may be used to achieve sufficient levels of transfection. In an aspect, the method disclosed by Woltjen et al [Nature 458: 766-70, 2009] for reprogramming somatic cells using a virus-free piggyBac transposon system (PB) may be used to generate AF cells. In an aspect, a construct disclosed by Kaji et al [Nature 458:771-5, 2009] may be used in which the four reprogramming genes are combined into one polycistronic transgene permitting production of the four proteins separately in stoichiometric amounts from a single RNA.

The concentration of AF cells used to generate AF tissue for an intervertebral disc implant disclosed herein will depend on the method of generation. As an example, for a bioreactor, in particular a spinner bioreactor, the concentration is generally in the range of about $0.1\times10^5$ cells/ml to $10\times10^6$ cells/ml, $2\times10^5$ cells/ml to $10\times10^5$ cells/ml, $4\times10^5$ cells/ml to $8\times10^5$ cells/ml, in particular $4\times10^5$ cells/ml to $6\times10^6$ cells/ml, more particularly $1\times10^6$ cells/ml.

The AF cells may be grown on a polymeric scaffold to generate the second construct. In an aspect the polymeric scaffold comprises synthetic polymers. The use of scaffolds comprising synthetic polymers generally provides a number of advantages including without limitation, greater control of the biodegradation rate and more gradual changes in mechanical properties with time, less batch-to-batch variability, more versatility in sterilization protocols, no risk of disease transmission, and/or minimal if any issues with respect to immune responses to antigenic material.

The second substrate for growing AF tissue may be a scaffold composed of silk fibroin, a protein polymer made by silkworms. For example, the second substrate may be the porous silk scaffold described in Chang et al, European Spine Journal, 16(11): 1848-1857, 2007. A silk scaffold may be chemically modified with arginine-glycine-aspartic acid peptide.

In an aspect, the scaffold comprises elastomeric polymers, such as polyurethane fibres. Because of their segmented block co-polymeric nature, urethane elastomers may be formulated to exhibit a wide range of physical properties making them particularly suitable for tissue engineering purposes [See, Santerre, et al, Biomaterials 26: 7457-70, 2005]. In a particular aspect, the scaffold comprises polycarbonate urethane (PU) fibres. Polycarbonate-based PUs may be particularly useful for generating AF tissue since they incorporate carbonate bonds into their structure and degrade into alcohols and carbon dioxide, a soluble gas that can easily dissolve in the biological environment [See, Tang et al, J Biomed Mater Res 57: 597-611, 2001 and Tang et al, Biomaterials 24: 2003-11, 2003]. In addition, polycarbonate-based PUs do not produce acid by-products (associated with polylactic acid (PLA) and other degradable polyesters) that lower the pH and may damage tissue by eliciting an inflammatory response from the host and affecting cell function.

The surface of the polymeric substrate for growing AF tissue may be modified. In an aspect, the polymeric substrate is modified with additive(s) that enhance cell/protein interactions with the polymeric scaffold. In a particular aspect, the polymeric substrate comprises PUs containing anionic/dihydroxyl oligomeric (ADO) additives that enhance cell/protein interactions with the scaffold. Such designed ADO molecules may be used to enhance or substitute for other approaches used to enhance surface energy and thereby protein and cell adhesion. Other approaches include, without limitation, the chemistry of the base polymer, mixing different base polymers to generate the fibres, the introduction of different block segments into the base polymer fibre, the dimensions of the polymeric fibres, or the surface topography of the fibres (i.e. spacing between them, random vs oriented.

In a particular embodiment, the scaffold comprises electrospun aligned polycarbonate urethane (PU) fibres. In an embodiment, the scaffold comprises polycarbonate urethane (PU) fibres electrospun onto a suitable mandrel (e.g. tubing) resulting in aligned, nanofibrous polymer scaffolds. The scaffolds may have a thickness of up to about 100, 150, 200, 250, 300, 350 or 440 µm, in particular between about 200 and 300 µm, more particularly 150 µm. The fibre diameter can range on average between about 10 to 500 nm, 25 to 500 nm, 50 to 500 nm, 50 to 400 nm, 50 to 300 nm, 100 to 500 nm, 100 to 400 nm, 100 to 300 nm, more particularly 100 to 300 mm. The tensile strength of the aligned PU-ADO scaffold may be in the range of about 1 to 20 MPa, 5 to 10 MPa, 6 to 20 MPa, 6 to 8 MPa, in particular 7 MPa which is within the same order of magnitude as native AF lamella [Ebara et al, Spine (Phila Pa. 1976), 21(4):452-61, 1996]. The scaffold is optionally capable of withstanding strains of about 25%, 30%, 40% or 50% or greater before breaking, in particular 40% or greater before breaking. The AF physiological strain in vivo may be less than about 10%, 15%, or 20%, in particular 15% [See, Lotz et al, Spine (Phila Pa. 1976) 23: 2493-506, 1998 for an in vivo mouse model of compression-induced degeneration]. In a particular embodiment, the scaffold has a thickness of 50 to 300 µm and comprises electrospun aligned polycarbonate urethane (PU) fibres with a fibre diameter of about 10 to 300 nm and optionally (a) a tensile strength in the order of magnitude of native AF lamella (e.g., 7 MPa); (b) capable of withstanding strains of 40% or greater before breaking; and/or (c) a physiological strain in vivo less than 15%.

AF tissue grown on a scaffold disclosed herein is generally characterized by one or more of the following properties:

1. actin cytoskeleton oriented parallel to the long axis of the cell mimicking the actin organization in AF cells during tissue development and in fully formed tissue.
2. Type I collagen, the major matrix molecule of AF tissue, is present throughout tissue
3. Type I collagen initially, is oriented parallel to the cell and fibrillar fibronectin (also present in the developing AF).
4. collagen fibres extending out of the cell in a polarized manner similar to human AF cells in vivo;
5. where more than one layer of AF/scaffold is present, layers of AF tissue/scaffold are adherent to each other.

AF layers may be generated by placing two AF/synthetic elastomeric scaffolds on top of each other such that the fibre orientation forms an oblique angle (for example, from 20 to 70 degrees) to each other. This dual layered arrangement is then wrapped around the NP component multiple times to build up successive layers that are at alternating orientation to each other.

An implant disclosed herein may comprise a multi-lamellate AF comprising layers of AF tissue on and integrated with a scaffold arranged at oblique angles to each other. A multi-lamellate AF may comprise 2 or more layers (i.e. dual AF/scaffold layers), 3 or more layers, 5 or more layers, 8 or more layers, or 10 or more layers. A multi-lamellate AF (2 or more layers) may be generated by seeding AF cells in a dynamic flow bioreactor or in static culture. In an aspect, AF scaffold strips are seeded with cells and grown in static culture for 48 hours prior to placement in a bioreactor. Alternatively the scaffold may be rolled around a mandrel (e.g. tube), and in a bioreactor it is seeded with AF cells and grown for up to 2 weeks, in particular for 24 hours, 48 hours, 3 days, 4 days, 5 days or 6 days, or up to 1, 3, 4, 5 or 6 weeks, optionally up to 2 weeks. The multi-lamellate AF may be characterized by the following properties:

1. Cells and collagen aligned parallel to scaffold fibers.
2. Presence of collagen (predominantly type I collagen) diffusely throughout the tissue.
3. Lamellar layers are integrated,
4. Peel test to examine strength of integration is at least 0.03 N/mm compared to native bovine AF of 0.6 N/mm.

In a particular aspect, the multi-lamellate AF is formed as a donut shape with a 2-20 mm, 2-15 mm, 5-20 mm, 5-15 mm, 10-20 mm, 2-10 mm, 2-9 mm, 3-9 mm, 4-8 mm, 3-5 or 2-5 mm diameter hole.

First Construct

The first construct comprising regenerated NP tissue may be prepared by culturing isolated nucleus pulposus cells on a substrate (also referred to as a first substrate when the scaffold of the second construct is referred to as a second substrate). NP precursor cells (e.g, MSC, embryonic stem cells, and iPS) may also be used as a source of NP cells to prepare the first construct.

In an embodiment, the NP cells or precursor cells may be first cultured for example on a porous tissue culture insert and then transferred to the substrate. An example of such an insert is the tissue culture insert known as Millicell CM®, (Millipore Corp., Bedford, Mass., U.S.A.), optionally coated with an attachment factor, including without limitation type II collagen (Sigma Chemical Co., St. Louis, Mo., U.S.A.).

The substrate may be selected from bone or an engineered biomaterial [see, U.S. Pat. No. 8,163,554]. In an aspect, the first substrate is a bone substitute, in particular an engineered bone substitute such as coral derivatives (Interpore International Inc., Calif.), deproteinized bovine bone (Bio-oss®, Geistlich Biomaterials, Switzerland) or a porous biodegradable biomaterial. In a particular aspect the bone substitute is a biodegradable porous ceramic, more particularly a porous ceramic formed by sintering calcium polyphosphate (CPP) powders generated from calcium and phosphate [Pilliar et al, Biomaterials 22: 963-72, 2001; Grynpas et al, Biomaterials 23: 2063-70, 2002; Shanjani et al, J Biomed Mater Res B Appl Biomater.; U.S. Pat. Nos. 7,494,614 and 6,077,989; Waldman et al, J Biomed Mater Res, 62(3): 323-30, 2002]. The CPP substrate is particularly useful as it supports tissue formation in vitro, has strength similar to bone, and when implanted in vivo bone grows into the pores rapidly fixing it in place (e.g. bone ingrowth of about 1 cm in 1 month).

The NP cells are grown in growth media and under suitable conditions so that the cells maintain their phenotype, accumulate extracellular matrix and form a continuous layer of tissue on the substrate. The cultured NP tissue has similar characteristics to native NP tissue in terms of proteoglycan content and mechanical properties such as equilibrium stress, equilibrium modulus, and hysteresis [see, Seguin C A et al. Spine 29:1299-306, 2004.].

In an aspect, a triphasic NP construct was used as the first construct in an intervertebral disc implant disclosed herein comprising nucleus pulposus tissue, cartilage tissue and a substrate. The cartilage tissue can be considered a cartilage endplate of the implant. In a particular aspect, the triphasic construct comprises a continuous layer of nucleus pulposus tissue adherent to underlying cartilaginous tissue integrated with the substrate, in particular a bone substitute such as a porous calcium polyphosphate (CPP) bone substitute. The triphasic construct may be formed by growing cartilage tissue on the first substrate in vitro and placing nucleus pulposus cells onto the in vitro-formed cartilage. Under suitable conditions, NP cells maintain their rounded morphology and form a continuous layer of NP tissue adherant to the underlying cartilage tissue which is integrated into the substrate. Examples of suitable culture media are known in the art, such as Hams F12 and/or Dulbecco's modified Eagle's medium (DMEM). The culture medium may contain serum, for example, heat inactivated fetal bovine serum in a concentration range of about 2-20%, optionally 10-20%, and may further contain growth factors or insulin-transferrin-selenium (ITS), or ITS plus bovine serum albumin and linoleic acid and ascorbic acid or ascorbate-6-phosphate. The cells may be cultured at 37° C. in a humidified atmosphere supplemented with CO2. In an aspect, the cells are grown in a suitable medium such as DMEM containing 10% fetal bovine serum and ascorbic acid (100 μg/ml, final concentration).

Cartilage tissue or the cartilage endplate can be formed on, and integrated with, the substrate using the method described in U.S. Pat. No. 5,326,357, U.S. Pat. No. 6,464,729 or described herein. In an aspect, the cartilage tissue or cartilage endplate comprises a calcified cartilage tissue or a bizonal cartilage tissue comprising a continuous layer of cartilage tissue engineered on a substrate interfaced via a zone of calcified cartilage tissue. The calcified cartilage tissue or calcified interface of a bizonal cartilage tissue has characteristics of healthy articular cartilage-subchondral bone interface in vivo, in particular accumulation of collagen type X and mineral in addition to collagen type II and proteoglycans.

A calcified cartilage tissue or bizonal cartilage tissue may be prepared using chondrocytes isolated from articular cartilage from animals, optionally humans, bovines, ovines, rabbits, most particularly humans. The chondrocytes may be isolated from adult or fetal tissue. The chondrocytes may be isolated by sequential enzyme digestion techniques, such as those described in Kandel et al, Biochem. Biophys. Acta. 1035:130, 1990. For example, the cartilage may be treated with 0.5% protease followed by 0.04% bacterial collagenase.

Alternatively, a calcified cartilage tissue or bizonal cartilage tissue may be prepared using chondrocyte precursor cells such as bone marrow stromal cells (BMSCs). BMSCs may be used to generate BMSCs with chondrogenic potential using methods known in the art (see for example, Chase L G, et al, Stem cells translational medicine. 2012; 1:750-8; Gottipamula S, et al, J Tissue Eng Regen Med. 2013). In an aspect, bone marrow stromal cells are isolated from bone marrow, optionally expanded, and cultured in 3-dimensional culture in chondrogenic media (e.g. hgDMEM, insulin-transferrin-selenium cell culture supplement, dexamethasone, ascorbic acid, and transforming growth factor-β3) to generate chondrocytes (predifferentiated chondrocytes, PDC).

Suitable substrates for culturing the chondrocytes include, without limitation, the substrate described herein, in particular bone or engineered biomaterial, optionally a CPP substrate. The substrate may be optionally coated with compounds or molecules that enhance cell and/or protein interactions with the substrate or cell metabolism, such as hydroxyapatite. The chondrocytes can be seeded on the substrate at a cell density of about to $1 \times 10^5$ to $1 \times 10^7$ cells/cm$^2$, optionally $1 \times 10^6$ cells to $8 \times 10^6$ cells/cm$^2$, particularly $1 \times 10^6$ cells to $2 \times 10^6$ cells/cm$^2$. The chondrocytes seeded on the coated or uncoated substrate are grown in suitable culture media [e.g., Ham's F12 and/or Dulbecco's modified Eagle's medium (DMEM)] with a mineralization agent. Suitable mineralizing agents include beta-glycerophosphate, ATP, phosphoethanolamine, and triiodothyronine (T3). In some embodiments using chondrocytes differentiated from bone marrow stromal cells T3 may be selected as the mineralizing agent. The concentration of the mineralizing agent is selected to provide a desired amount of mineralization. By way of example, the amount of T3 which may be used in the method is about 1 to 5 nM. The mineralizing agent is generally applied to the cultures for 2 to 21 days after initially seeding the chondrocytes.

The mineralizing agent may be removed after 4 to 10 days, in particular 4 to 6 days, more particularly 4 days. Chondrocytes may be subsequently seeded on top of the calcified cartilage tissue to generate a bizonal cartilage tissue comprising a continuous layer of cartilage tissue on a substrate interfaced with a zone of calcified cartilage. The multi-bizonal cartilage tissue constructs may be maintained in culture under the same culture conditions as the calcified cartilage tissue but in the absence of the mineralizing agent, such as T3.

In an aspect, chondrocytes (articular or differentiated) are placed on the top surface of the substrate, (optionally a porous CPP substrate) which optionally comprises calcified cartilage tissue, and allowed to form cartilage tissue, NP cells are placed onto the in vitro-formed cartilage and grown for up to 1 week, in particular for 24 hours, 48 hours, 3 days, 4 days, 5 days or 6 days, or up to 2, 3, 4, 5 or 6 weeks, 2-10 weeks, 4-10 weeks or 6-8 weeks, to form a continuous layer of NP tissue adherent to the cartilage tissue which is integrated with the substrate, optionally the porous CPP substrate [see, Hamilton et al, Biomaterials 27(3): 397-405, 2006 for a process for forming a triphasic construct].

Preparation of Intervertebral Disc Implant

An intervertebral disc implant disclosed herein may be generated by wrapping the second construct comprising one or more layers of regenerated AF tissue which is on and adherent to the scaffold (which can also be referred to as a second substrate) around the first construct comprising regenerated NP tissue on and integrated with the substrate (also referred to as first substrate when scaffold referred to as second substrate), in particular a bone substitute. In some aspects, the first construct may additionally comprise a continuous layer of cartilage tissue (i.e., calcified cartilage tissue or bizonal cartilage tissue) and the NP tissue is on and adherent to the cartilage tissue on the substrate. In some aspects, a second construct comprising two or more layers of in vitro formed-AF tissue/scaffold are wrapped around a triphasic first construct comprising nucleus pulposus tissue, cartilage tissue and the substrate, in particular a bone substitute.

An intervertebral disc implant disclosed herein may be generated by preparing the first construct comprising regenerated NP tissue which is on or integrated with a substrate, preparing the second construct comprising one or more layers of regenerated AF tissue which is on and adherent to a scaffold, and combining the first construct and second construct so that the second construct surrounds the first construct and the AF tissue and NP tissue are adjacent. In an aspect the second construct is in a shape which is adapted to receive the first construct so that the second construct surrounds the first construct and the AF tissue and NP tissue are adjacent. In an aspect the second construct is a donut-shape with a cylindrical hole extending through the center and the first construct is inserted in the cylindrical hole. The combined first and second constructs are cultured to generate the implant. Using an Instron tester at 0.1 Hz, 1% to 10% strain for 20 cycles the % hysteresis was on average 64.3% for the combined constructs. Using sequential step compressions of 1% strain to a maximum of 10% strain, the elastic modulus was on average 0.017 MPa.

The second construct may be cultured under suitable conditions prior to combining with the first construct. In an aspect, the second construct is first cultured for about up to 1 week, in particular for 24 hours, 48 hours, 3 days, 4 days, 5 days or 6 days, or up to 2, 3, 4, 5 or 6 weeks, optionally up to 2 week, in a bioreactor, in particular a spinner or flow bioreactor.

The combined first and second constructs may be grown in culture under suitable conditions. For example, they may be grown in a bioreactor for up to 1 week, in particular for 24 hours, 48 hours, 3 days, 4 days, 5 days or 6 days, or up to 2, 3, 4, 5 or 6 weeks, optionally up to 1 week. In an aspect, the combined constructs are grown in a bioreactor, in particular a spinner reactor which can rotate between about 10 and 90 rpm/min, about 10 to 40 rpm, or 20 to 30 rpm, in culture media under standard tissue culture conditions. Examples of suitable culture media are known in the art, such as Hams F12 and/or Dulbecco's modified Eagle's medium (DMEM). The culture medium may contain serum, for example, heat inactivated fetal bovine serum in a concentration range of about 2-20%, optionally 5-20%, and may further contain growth factors and or ITS, and optionally ascorbic acid or ascorbate-6-phosphate. In an aspect, the cells are grown in a suitable medium such as DMEM containing 10% fetal bovine serum and ascorbic acid (100 µg/ml, final concentration). The cells may be cultured at 37° C. in a humidified atmosphere supplemented with $CO_2$.

FIG. 20A-C illustrates an intervertebral disc implant 110 in accordance with an embodiment of the disclosure. In the illustrated embodiment, the first construct 112 comprises a continuous layer of nucleus pulposus tissue 114 directly on and integrated with the subsurface 116 of a substrate 118, such as a porous bone substitute. The second construct 120 comprises continuous layers 122, 124 of annulus fibrosus tissue on and adherent to scaffold. The layers 122, 124 have fibres 126, 128 that are angled obliquely to each other. The second construct 120 is wrapped around and surrounds and is integrated with the continuous layer of nucleus pulposus tissue 114 of the first construct 112. The substrate 118 protrudes from the NP 114 and second construct 120.

FIG. 21A-C illustrates another embodiment of the implant 210. In the illustrated embodiment, the first construct 212 comprises a continuous layer of nucleus pulposus tissue 214 on and adherent to cartilaginous tissue 230, which is on and integrated with a substrate 218, such as a porous bone substitute. Thus the NP tissue 214 is indirectly on and integrated with the subsurface of substrate 218 and the cartilaginous tissue 230 is between the substrate 218 and the NP tissue 214. The second construct 220 comprises continuous layers 222, 224 of annulus fibrosus tissue on and adherent to scaffold. The layers 222, 224 have fibres 226, 228 that are angled obliquely to each other. The second construct 220 is wrapped around and surrounds and is integrated with the continuous layer of nucleus pulposus tissue 214 and the cartilaginous tissue 230 of the first construct 212. The substrate 218 protrudes from the NP 214 and second construct 220. In an embodiment, the cartilaginous tissue 230 comprises a calcified cartilage tissue or a bizonal cartilage.

In the embodiments shown, the second construct includes two layers of the AF tissue/scaffold. In alternative embodiments, the second construct can include two or more, three or more, four or more or five or more layers of the AF tissue/scaffold.

Methods and Kits

An implant disclosed herein has compositional properties similar to native intervertebral discs, in particular it is able to sustain loads immediately upon implantation. In addition, an intervertebral disc implant disclosed herein may integrate with native endplate on the opposite side or the substrate integrate with native bone.

In use, the intervertebral disc implants disclosed herein are implanted using surgical techniques known to those skilled in the art. The existing entire disc or a part thereof along with adjacent bone may be excised and replaced with at least one intervertebral disc implant disclosed herein. An intervertebral disc implant disclosed herein can be implanted into a site exposed by surgical resection, or alternatively endoscopic, laparoscopic or arthroscopic methods may be used to implant the disc. Subjects or patients to be treated using an intervertebral disc implant include mammals, optionally humans. A subject may be suffering from degenerative disc disease, neck or lower back pain, or trauma to the disc or vertebral body.

Also provided herein is use of the bizonal cartilage constructs or calcified cartilage constructs for repairing cartilage or cartilage end plates of the vertebral body. Further provided is the bizonal cartilage constructs constructs or calcified cartilage constructs disclosed herein for use in repairing cartilage or vertebra cartilage end plates. Even further provided is a method of repairing cartilage or vertebral body cartilage end plates comprising inserting the bizonal cartilage constructs or calcified cartilage constructs disclosed herein to replace damaged cartilage or vertebra cartilage end plates in the subject in need thereof. Also provided is use of the bizonal cartilage constructs or calcified cartilage constructs in the formation of the intervertebral implants disclosed herein. In an embodiment, the bizonal cartilage constructs or calcified cartilage constructs for use in the methods and uses disclosed herein is derived from stem cells.

The disclosure also contemplates kits comprising an intervertebral disc implant disclosed herein, in particular, a packaged sterilized intervertebral disc implant. A kit may optionally comprise a carrier for the implant and/or instruments for implanting the disc, for example, an adapter to retain or hold the implant and an implant tool, engaging the adapter, for inserting the disc into the implantation site and other instrumentation as required to prepare the bone and disc space to receive the implant.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

The following describes methods for producing the components of an intervertebral disc implant as disclosed herein.
Polyurethane Scaffolds (PU-ADO Scaffolds)

Degradable polycarbonate urethane (PU) blended with ADO enhances AF cell adhesion making it an advantageous polymer [Yang et al, J Biomed Mater Res A. 91:1089-99, 2009]. However, it can be used in the absence of ADO supplementation. Furthermore it is electrospun onto a specially designed mandrel resulting in aligned, nanofibrous polymer scaffolds up to 250 µm thick. Fibre diameter ranged on average between 10 to 500 nm. Degradation rates in the presence of cholesterol esterase (a monocyte-derived enzyme) showed uniform PU breakdown (7 wt % mass loss/week) which would yield complete resorption of the scaffold within 6 months. The tensile strength of the aligned PU-ADO scaffold was 7 MPa; within the same order of magnitude as native AF lamella [Ebara et al, Spine (Phila Pa. 1976), 21(4):452-61, 1996]. The polymer scaffold can withstand strains of 40% or greater before breaking; AF physiological strain in vivo is less than 15% [Lotz et al, Spine (Phila Pa. 1976) 23: 2493-506, 1998]. The annulus fibrosus cell-seeded polyurethane nanofibrous scaffold is organized to form an aligned integrated multi-lamellated tissue wherein each lamellae is at an oblique angle to each other.
Nucleus Pulposus (NP) Tissue-Bone Substitute Conditions to form a continuous layer of NP tissue on and integrated with the immediate subsurface of a bone substitute have been developed (see U.S. Pat. No. 8,163,554; Hamilton, Biomaterials 27(3): 397-405, 2006; and FIG. 3). The NP has similar characteristics to native bovine NP in terms of proteoglycan content and mechanical properties such as equilibrium stress, equilibrium modulus, and hysteresis. The bone substitute used in this example is a biodegradable, porous ceramic formed by sintering calcium polyphosphate (CPP) powders which had been generated from calcium and phosphate. The CPP substrate supported tissue formation in vitro, had strength similar to bone, and when implanted in vivo bone grew into the pores rapidly fixing it in place (bone ingrowth of approximately 1 cm in 1 month). There was no adverse reaction to the bone substitute as long as 9 months post implantation.

Figure 4A:
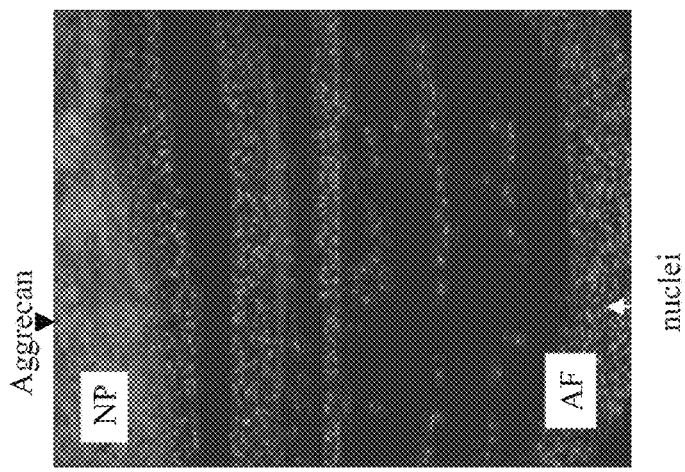
FIG. 4 shows AF and NP disc tissue immunostained for the major macromolecules that make up this tissue. (A) In vitro formed disc tissue has been immunostained for major components of native IVD (collagen type I (red), collagen type II (green), and cell nuclei or (B) aggrecan and cell nuclei. (fluorescent immunostaining and immunofluorescent light microscopy, size bar for these pictures is 10 µm). Type II collagen and aggrecan are present in the nucleus pulposus and type I collagen is present in the annulus fibrosus. The green dots seen in images of col II stained tissue are artefact and represent precipitate. NP=nucleus pulposus; AF=annulus fibrosus.
Figure 4A:
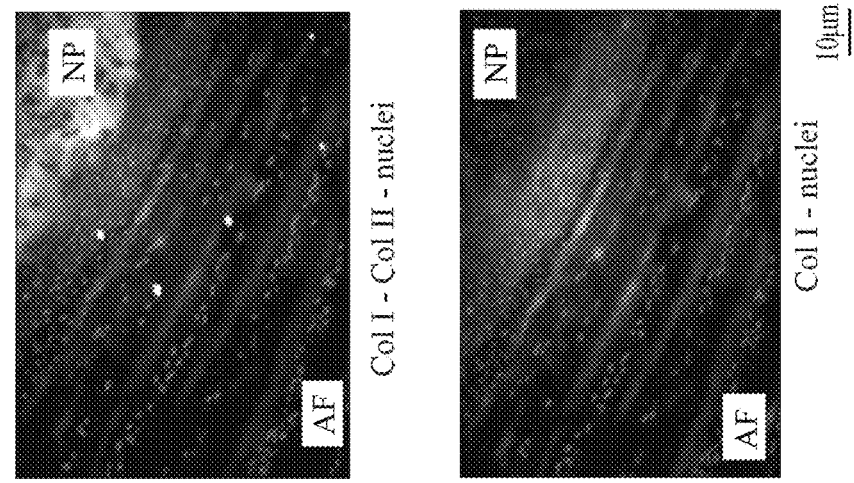
Figure 4B:
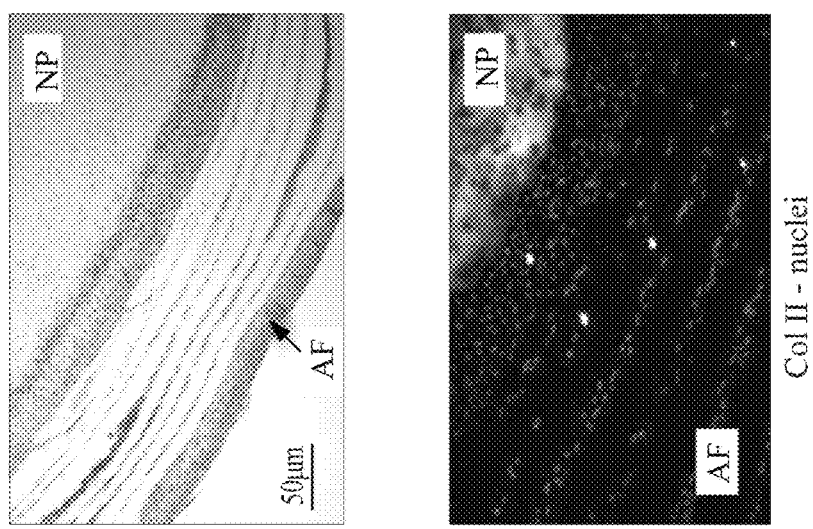
Figure 5:
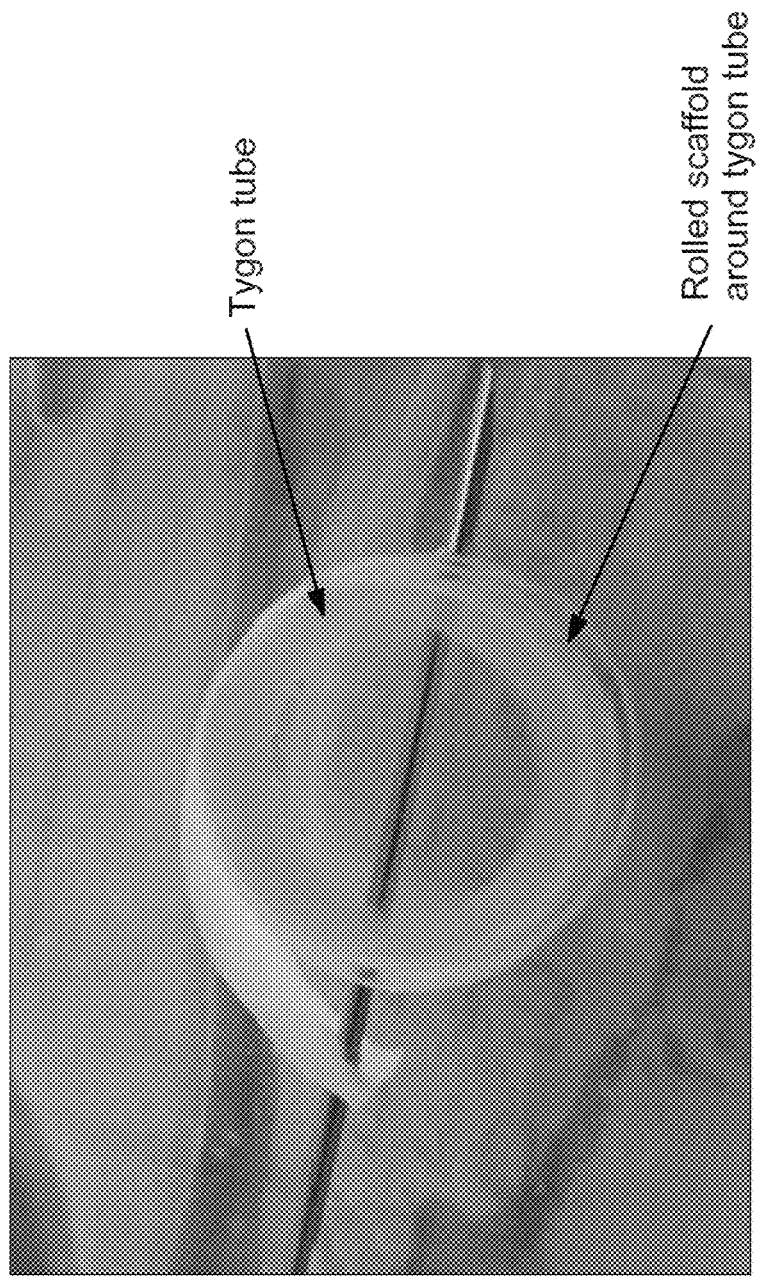
FIG. 5 shows the gross appearance of a scaffold rolled around tygon tubing before cell seeding.

A continuous layer of nucleus pulposus tissue adherent to underlying cartilaginous tissue which was integrated with porous calcium polyphosphate (CPP) formed a triphasic construct. (NP-CCP-bone substitute) [Hamilton et al, 2006, supra]. The presence of a cartilage layer enhanced the interfacial shear strength of the tissue to the bone substitute.
AF Tissue Formation A single AF lamella was formed using either primary or passaged AF cells, and PU nanofibrous scaffolds. Cells isolated from the outer AF of bovine caudal discs and grown on aligned PU-ADO scaffolds coated with fibronectin and experiencing strain, assumed a spindle shape with orientation parallel to the fibres. Confocal microscopy following phalloidin staining showed that the actin cytoskeleton was oriented parallel to the long axis of the cell mimicking the actin organization in AF cells during tissue development and in fully formed tissue. At the early time points Type I collagen, the major matrix molecule of AF tissue, was organized parallel to the cell and fibrillar fibronectin (also present in the developing AF) was present. Transmission electron microscopy showed collagen fibres extending out of the cell in a polarized manner similar to human AF cells in vivo. Electrospun PU is an ideal scaffold as AF cells grown on this biomaterial maintain phenotype and form tissue that mimics the developing AF in vivo. The OAF (outer AF) cells accumulate type I collagen and inner AF cells accumulate both type I and II collagen, characteristic of the native AF. (Iu J et al Tissue Engineering, in press, 2014). Seeding scaffolds with combined inner and outer AF cells generated even thicker tissue. To generate multi-lamellate AF (i.e. two or more AF/scaffold dual layers) two methods were investigated. AF scaffold strips were placed flat in a custom designed Teflon holder (FIG. 17), seeded with cells and grown in static culture for up to 48 hours and then rolled and placed in a bioreactor, spinner or flow. Alternatively the scaffold was rolled around a perforated teflon tube (FIG. 4), and seeded with AF cells and grown within a spinner bioreactor for up to 3 weeks. Histological examination at 3 weeks of culture showed tissue formation and integration of the layers of the scaffold using either method. However in the cell-seeded flat strips the integration was inconsistent. In addition more tissue formation was observed in the scaffolds grown in a bioreactor compared to prolonged static culture. The cells and collagen were aligned parallel to scaffold fibers. Trichrome staining showed the presence of collagen diffusely throughout the tissue which was predominately type I collagen, as demonstrated by immunostaining. Collagen content increased significantly over the 3 weeks. These studies suggest growing the multi-lamellated PU scaffold in a dynamic bioreactor with the construct not moving using a combination of inner and outer AF cells.

In a particular method, the multi-lamellate AF tissue is formed as a donut with a 4 mm diameter hole generated as follows. AF cells ($5 \times 10^5$ cells/ml, cell density of native AF is ~$9 \times 10^6$ cells/cm$^3$) isolated from bovine caudal spines (6-9 months of age) were resuspended in DMEM supplemented with 10% fetal bovine serum and ascorbic acid (100 ug/ml) and grown up to 4 weeks. To generate tissue that most closely mimics the native AF, the bioreactor rotation rate employed was 10 to 90 rpm, optionally about 30 rpm to allow for cell adhesion i.e., not disrupted by rotation speed.

IVD Tissue Interfaces

Figure 3:
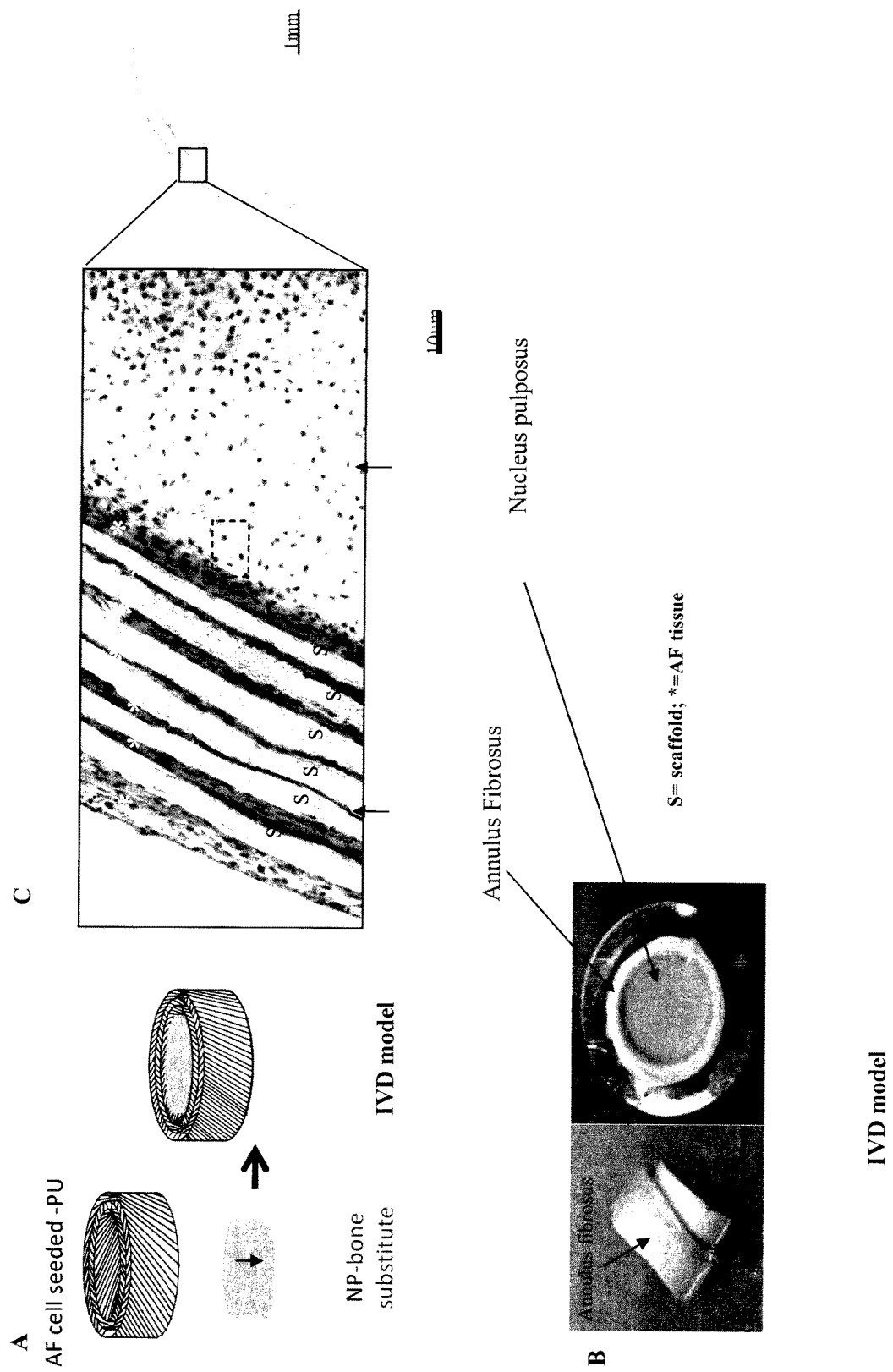
FIG. 3 shows (A) a schematic line diagram showing the concept of forming the intervertebral disc; (B) the gross appearance of the in vitro formed IVD (lateral aspect and top) after 2 weeks in combined culture (1 cm diameter); and (C) light microscopic appearance of annulus fibrosus (AF) and nucleus pulposus (NP) which shows integration (see dashed box). As well the AF lamellae are integrated. Please note differences in tissue thickness between the scaffold lamellae are likely a result of the angle of sectioning. * indicates AF tissue; S=scaffold.
Figure 6:
FIG. 6 shows a spinner bioreactor with intervertebral disc implants of the disclosure at the bottom.
Figure 17:
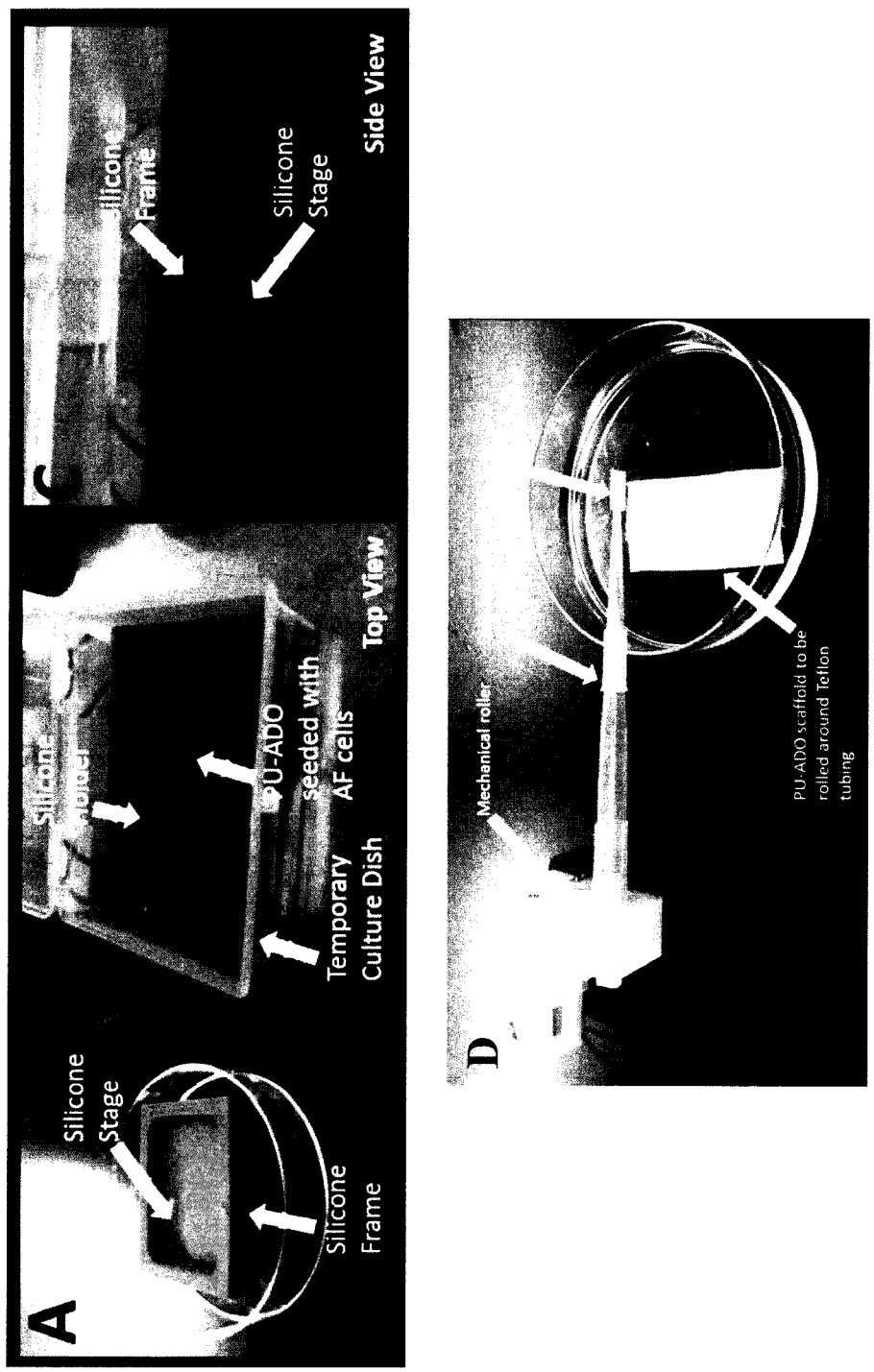
FIG. 17 shows a holder (silicone stage and frame) specifically designed for flat seeding of the PU membrane. The silicone frame (A) vertically does not fit into a standard 10 cm culture dish and therefore a larger culture holder was designed (B-C). The silicone holder prevents leaking of media out of the center. (D) A mechanical roller was specifically made to roll the layers of scaffold. The roller is placed over a culture dish containing PU scaffold seeded with AF cells. A 200 μL pipette tip (in this sample but can be any size) is placed on the end of the roller to maintain sterility and the Tygon tubing is secured to the end of the pipette tip and the scaffold is mechanically rolled around it. The system is modular so various sizes of the tip can be accommodated.
Figure 18:
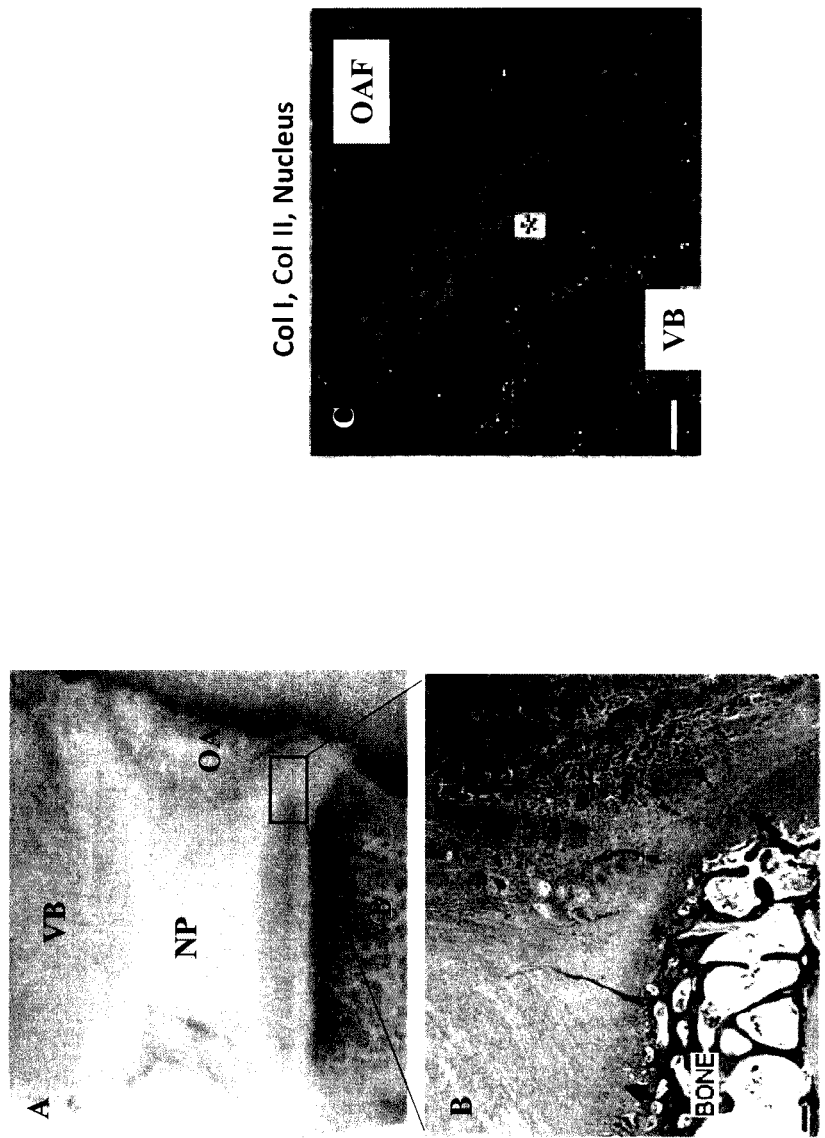
FIG. 18 shows gross appearance of an intervertebral disc and adjacent vertebral bodies (proximal and distal); B) Histological appearance of interface of intervertebral disc and bone of vertebral body. Arrows indicate cartilage endplate, * indicates insertion of AF (hematoxylin and eosin stained); C) Immunohistochemically stained section of this region showing collagen type 1 (red) in the AF, collagen type 2 in the cartilage endplate (green). Nuclei of cells are stained with DAPI and are blue.
Figure 19:
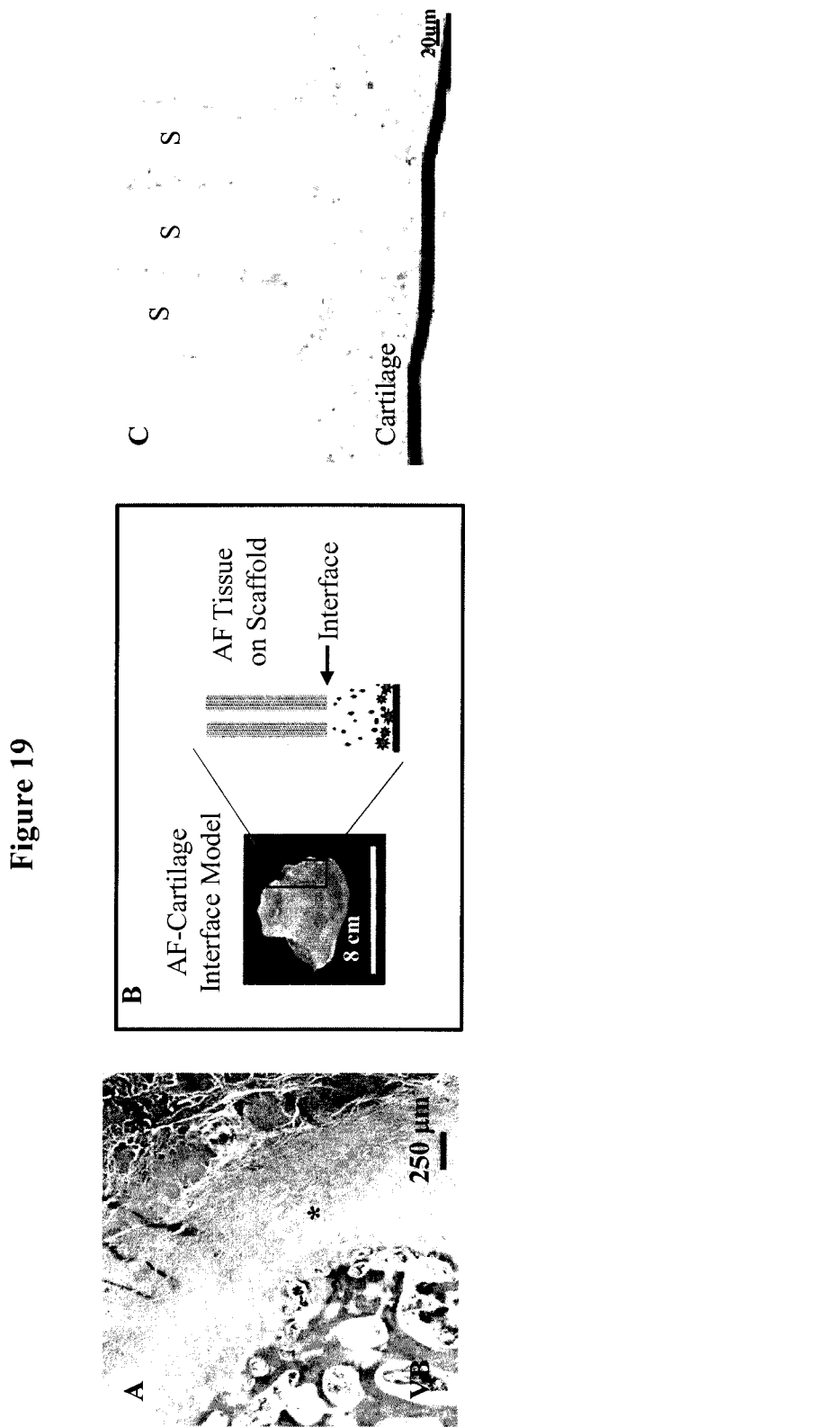
FIG. 19 shows A) Histological appearance of interface of native intervertebral disc and adjacent vertebral body (AF=annulus fibrosus tissue and VB=vertebral body, * indicates interface region); B) Gross appearance of AF tissue-scaffold integrated with cartilage tissue all formed in vitro. C) Histological appearance of the in vitro formed AF-cartilage interface (hematoxylin and eosin stained).

Up to 6 layers of in vitro formed-AF tissue/scaffold were wrapped around either the diphasic or the triphasic construct and the resulting unit was grown in culture for 2 weeks in a rotator bioreactor (spinner) to form an intervertebral disc implant (FIG. 3). The cell-seeded scaffold was wrapped aseptically around a Teflon tube by hand using forceps or alternatively using a specially designed electric roller, rolling in one direction at a speed ranging from 10 to 60 rpm/minute (FIG. 17). The electronic roller consisted of motor superglued onto a battery holder containing either 1 to 3 AA batteries (1.5V each). The motor shaft was extended with a pipette tip (10 to 1000 ul). The end of the scaffold was sealed with a non-toxic glue and the implant was placed in a spinner bioreactor which could rotate between 10 and 90 rpm/min in DMEM supplemented with fetal bovine serum (between 2.5 and 20%) and ascorbic acid (between 10 and 100 ug/ml). FIG. 3 shows an intervertebral disc implant generated in vitro after 1 week of combined culture showing the calcium polyphosphate substrate (CPP), nucleus pulposus tissue and annulus fibrosus tissue. FIG. 3 is a photomicrograph of the histological appearance of the in vitro formed intervertebral disc construct after one week in spinner bioreactor culture (FIG. 6) showing that the multi-layered annulus was integrated with the nucleus pulposus tissue.

Alternatively the AF scaffold can be placed in a flow bioreactor in the same media with a flow rate ranging from (0.05 to 10 ml/min). The cell-seeded scaffold was then grown in culture for up to 4 weeks. The scaffold was removed from culture, the tube was removed aseptically, and the nucleus pulposus-cartilage-CPP construct was placed in the hole (centre) and then placed back in culture. The combined construct (intervertebral disc) is placed back in culture and grown for an additional time up to 2 weeks and then evaluated or implanted.

Example 2

To Evaluate the Intervertebral Disc Implant in a Calf Model.

Under general anesthesia a paramedian incision was made on the dorsal (upper) side of the tail between the sacrocaudalis dorsalis medialis and lateralis muscles to expose the joint capsule of Cy4-5 intervertebral space in 4 month old calves. The disc space was identified using marker needles and ⅔ of the disc resected en bloc. Serum was collected from each animal for use as a media supplement for the culture system if an autogenous system was required. Multi-lamellated (up to 10 layers) AF tissue/scaffold (1 cm×1 cm) was formed under the optimal conditions using outer AF cells isolated from these discs. Alternatively the cells can be derived from another cow and an allogeneic system used, as was done in the examples shown.

One month later, using the same approach the AF of coccygeal discs proximal to the donor site was opened and a defect measuring approximately 1 cm×1 cm×0.5 cm was created leaving the outer AF layers intact. The implant, which, in this particular example, did not have a cartilage layer, was placed in the defect and the outer layer acted as a door to maintain the implant in the correct orientation and position. The outer layer was then closed by sutures. A total of 2 constructs per animal were implanted in the different discs of each tail. The muscle and skin were closed and the tail was wrapped with a bandage to minimize tail movement. This was left in place for one week and then removed to allow unrestricted movement. Muscle contraction, which applies much of the load in vivo, maintained the implanted tissue in place.

Figure 7:
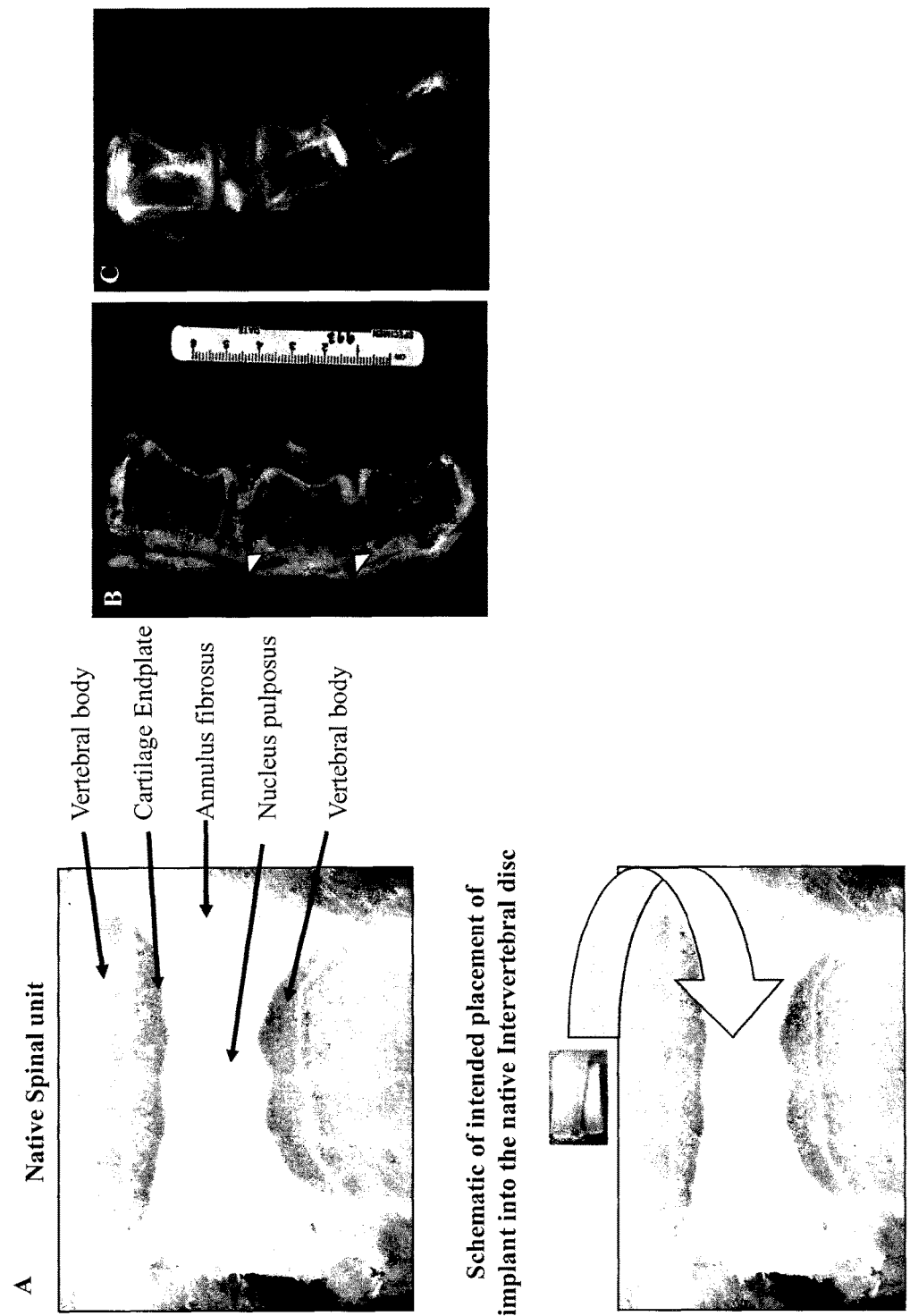
FIG. 7 shows (A) native bovine disc and adjacent vertebral bodies. The intended implantation site is indicated in the lower picture. (B) The bovine spine was harvested at 3 months after implantation and examined grossly. The implant was present (arrowhead). (C) Xray of the spine showing the disc implant present in the native disc (arrow). As it is a partial disc replacement, residual AF tissue is seen surrounding the implant.
Figure 8:
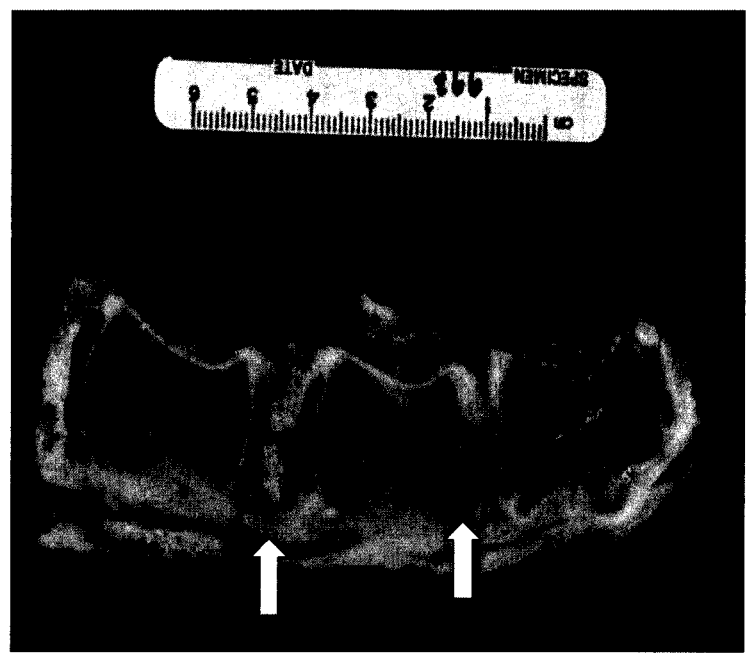
FIG. 8 shows an in vitro formed intervertebral disc implant implanted into a defect created in the cow caudal disc. The spine was harvested after one month and examined by X-ray (A) and gross examination (B). The arrows point to the disc implant.
Figure 8:
Figure 9:
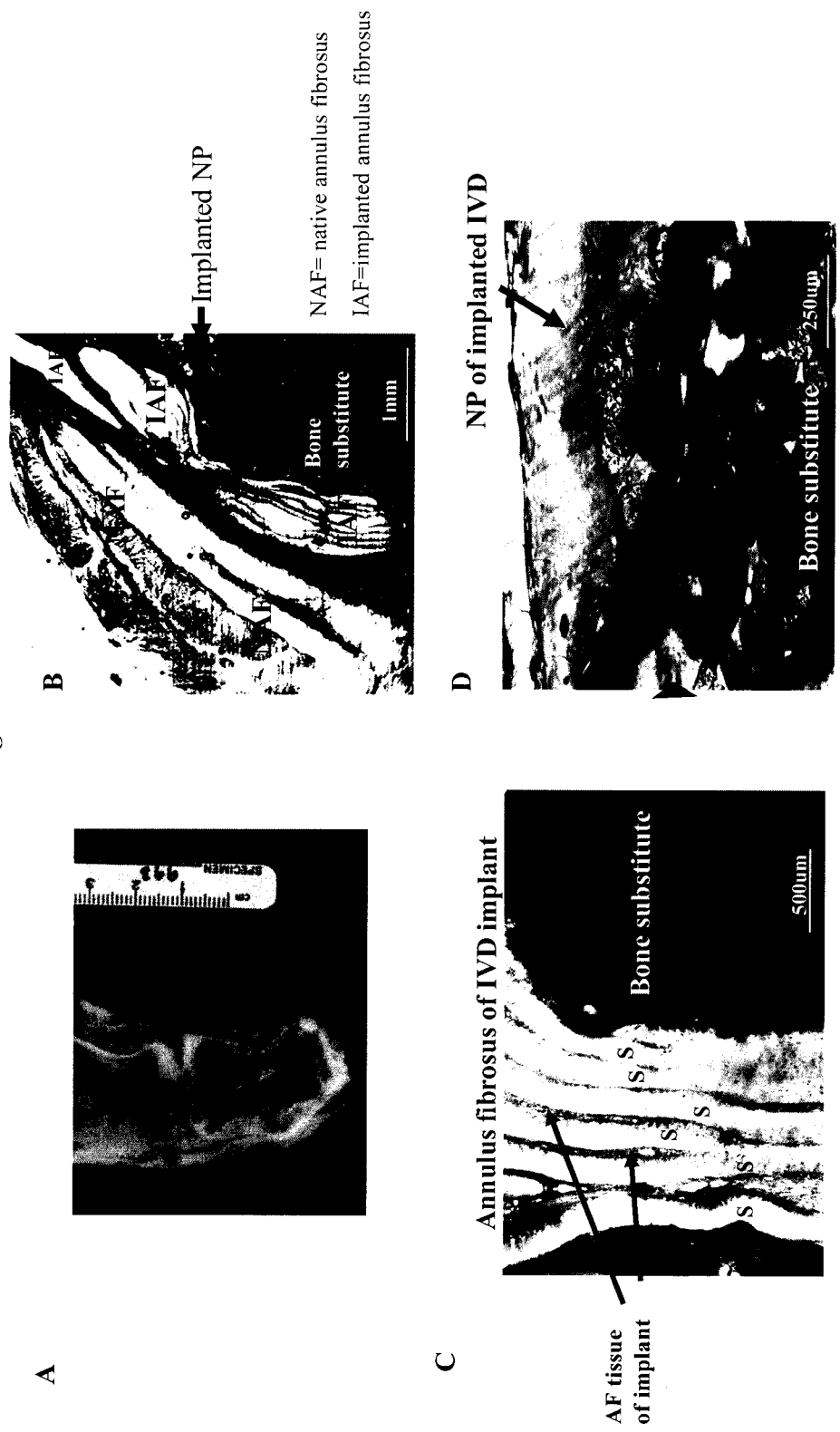
FIG. 9 (A) Dashed box indicates region where sample was taken for histological assessment from the spine. Implant indicated with arrow. (B) Histological appearance of implanted disc. The implanted nucleus pulposus is indicated with an arrow. The implanted annulus fibrosus is present adjacent to the nucleus pulposus and bone substitute (as occurs in native disc) and is integrated with the native bovine annulus. The diameter of the scaffold fibers are variable in part because of degradation but also because of the angle at which the tissue is sectioned relative to the implant. (C) Annulus tissue is seen between scaffold lamellae. (D) The implanted nucleus pulposus tissue is seen integrated to the bone substitute where it can be seen also within the pores of the bone substitute (arrowhead). It is noted that tissue shrinkage occurs with processing and this shrinkage does not occur uniformly in the different tissues. In this example, the AF tissue/scaffold was adherent to the bone substitute.

The implant with adjacent tissue was harvested at 1 and 3 months and evaluated macroscopically. FIG. 7 shows a successful partial disc replacement implant after one month and FIG. 8 shows an implant after three months. FIG. 9 shows the histological appearance of the intervertebral disc implant three months after implantation. The implant, as a partial disc replacement, was present within the bovine caudal disc and the bone substitute was in the bone. The implant was surrounded by and integrated with the outer most annulus fibrosus lamellae which served to hold the disc in place following implantation. The implant tissue was intact as was the bone substitute. A reparative response was seen in the bone adjacent to the implant which resulted in bone ingrowth into the bone substitute which aids in fixation of the implant. Furthermore, in this example, the AF tissue/scaffold was also adherent to the substrate (CPP bone substitute).

Example 3

Cell Sources for Generating NP and AF Tissues
Induced Pluripotent Stem Cells (iPS) Cells from NP Cells:

A method was developed to transfect bovine nucleus pulposus (NP) cells (approximately 40% efficiency) with a single PB cassette containing sox4, klf-4, c-myc, and oct4 [Munoz et al, Theriogenology, 69: 1159-64, 2008]. Approximately 25 days after transfection (and selection), primary colonies were detected. By one passage there was 1100 fold expansion of cell number. After five passages, the putative iPS colonies still stained positively for the pluripotency markers Nanog, TRA-1-60 and SSEA4 (stage-specific antigen 4) (all markers of bovine inner cell mast of a blastocyst-stage embryo from which ES cells are derived) [Munoz et al, 2008, supra]. In a preliminary study withdrawal of doxycycline early in colony formation resulted in a decrease in colony size and loss of staining for pluripotency markers suggesting that these cells are not yet fully committed iPS cells and may have the potential to revert back to their original phenotype and could be a way to easily redifferentiate the cells.

Mesenchymal Stromal Cells:

Methods have been developed to obtain MSC from bone marrow aspirates and differentiate them to chondrocytes and adipocytes under appropriate culture conditions. The colony-forming unit fibroblast (CFU-F) assay revealed that the frequency of clonogenic cells for first passage cells to be 1 in 2. As others have obtained MSC from bovine bone marrow [Mauck et al, Anat Rec (Hoboken); 290(1):48-58, 2007; Mauck et al, Biomech Model Mechanobiol. 6(1-2): 113-25, 2007], this methodology may be applied to other bone marrow aspirates to obtain mesenchymal stem cells suitable to use in the preparation of the intervertebral disc. The MSC cells can be differentiated towards chondrocytes using standard conditions to form the cartilage or co-cultured with nucleus pulposus cells or extracted nucleus pulposus matrix to form nucleus pulposus cells (Strassburg et al, Regen Med. 2010 September; 5(5):701-11. doi: 10.2217/rme.10.59. PubMed PMID: 20868326; Richardson et al, Stem Cells. 2006 March; 24(3):707-16. Epub 2005 Oct. 13. PubMed PMID: 16223853; Fang Z, et al, Biochem Biophys Res Commun. 2013 Mar. 15; 432(3):444-50. doi: 10.1016/j.bbrc.2013.01.127. Epub 2013 Feb. 12. PubMed PMID:23416353; Yuan et al, Biomaterials. 2013 May; 34(16):3948-61. doi: 10.1016/j.biomaterials.2013.02.004. Epub 2013 Mar. 5. PubMed PMID: 23465833; Vadalà G, et al, Spine (Phila Pa. 1976). 2008; 15; 33(8):870-6.; Le Visage et al, Spine (Phila Pa. 1976). 2006 Aug. 15; 31(18):2036-42.).

Example 4

Scaffold-Free Cartilage Tissue Engineering with a Mineralized Cartilaginous Interface to Porous Calcium Polyphosphate Substrate Using Bone Marrow Stromal Cells This example describes the successful engineering of an osteochondral construct which incorporates a zone of calcified cartilage at the cartilage-CPP interface using bone marrow stromal cells (BMSCs) as the cell source. A stepwise culturing strategy enabled the selective activation of BMSC-derived chondrocytes to induce mineralization at the interface-apposing zone, while avoiding such mineralization at the cartilage tissue above, thus conferring a bizonal organization to the cartilage tissue. The presence of the calcified zone increased the construct's interfacial shear strength that, based on gait data [Taylor W R, Poepplau B M, König C, Ehrig R M, Zachow S, Duda G N, et al. The medial-lateral force distribution in the ovine stifle joint during walking. Journal of orthopaedic research. 2011; 29:567-71; and Lee-Shee N K, et al, Veterinary and comparative orthopaedics and traumatology: VCOT. 2007; 20:70-2], should be sufficient to withstand the physiological load. Since BMSCs were expanded in media supplemented with autologous serum and the construct cultured in serum-free, defined media, this strategy is directly applicable to subsequent in vivo preclinical studies and thus bears clinical significance.

The following materials and methods were used in the study described in this example.

Materials and Methods

Chondrogenic Predifferentiation of BMSCs in Membrane Cultures

Sheep bone marrow stromal cells (BMSCs) were isolated and expanded from bone marrow aspirates [Lee W D, et al, Tissue engineering Part C, Methods. 2011; 17:939-48] in the expansion media (XM) that consists of minimum essential media α (αMEM) with pyruvate and glutamine (Wisent, St-Bruno, QC, Canada) and 10% (v/v) autologous serum. Autologous serum was generated by collecting blood from each sheep and clotting for 30 minutes. BMSCs were passaged with 1× TrypLE Select (Life Technologies, Burlington, ON, Canada). BMSCs were cryopreserved after first passage: after thawing, BMSCs were further expanded in monolayer for two passages.

To differentiate BMSCs to chondrocytes, $2.0 \times 10^6$ MSCs were seeded onto membranes (0.2 µm pore size; Millipore, Billerica, Mass., United States) coated with collagen type IV (Sigma-Aldrich, Oakville, ON, Canada) in PBS overnight. After 6 hours, XM was replaced with a defined chondrogenic media (CM) composed of high-glucose Dulbecco's modified Eagle medium with pyruvate and glutamine (hgDMEM; Life Technologies), 1× insulin-transferrin-selenium cell culture supplement (ITS; BD Biosciences, Bedford, Mass.), 100 nM dexamethasone (Sigma-Aldrich), 100 µg/mL ascorbic acid (Sigma-Aldrich) and 10 ng/mL transforming growth factor-β3 (TGF-β3; R&D Systems, Minneapolis, Minn., United States). Media was changed every 2-3 days. After 3 weeks of culture, BMSC-derived chondrocytes (termed herein as predifferentiated chondrocytes or PDCs) were isolated by digesting in 0.5% (w/v) collagenase (Roche Diagnostics, Indianapolis, Ind., United States) in F12 media with periodic agitation for 2 hours at 37° C.

Preparation of Porous CPP Substrates with a Hydroxyapatite Coating

Cylindrical CPP rods of 4 mm diameter were prepared by gravity sintering 75-150 µm CPP powder particles at 950° C. as previously described [Waldman S D, et al, Journal of biomedical materials research. 2002; 62:323-30]. Disks of 2 mm thickness were cut from the rods incubated in 1× phosphate-buffered saline (PBS) at 37° C. for 1 week, with the buffer changed every other day. Organic-route thin-film sol gel processing method was used to deposit a layer of hydroxyapatite on the CPP substrate [Gan L, et al, Part I: Synthesis and characterization. Biomaterials. 2004; 25:5303-12]. To synthesize the sol gel, triethyl phosphite (Sigma-Aldrich) was hydrolyzed for 24 hours in excess ddH$_2$O with vigorous stirring, and a stoichiometric amount (to maintain a Ca/P ratio of 1.67) of calcium nitrate tetrahydrate (Sigma-Aldrich) solution in 100% ethanol was added dropwise. The clear sol was aged at 40° C. for 4 days. Then, a half-volume of 100% ethanol was added and the sol was further aged at room temperature for 2 days. CPP disks were dipped into the sol gel sideways for 8 seconds and withdrawn at a speed of 20 cm/min, air-dried for 10 minutes and annealed for 15 minutes at 210° C. Disks were dipped again, annealed at 500° C. for 20 minutes and gradually cooled. The coated disks were placed in Tygon tubing to create a well-like structure and subsequently sterilized by γ-irradiation (2.5 MRad).

Figure 11:
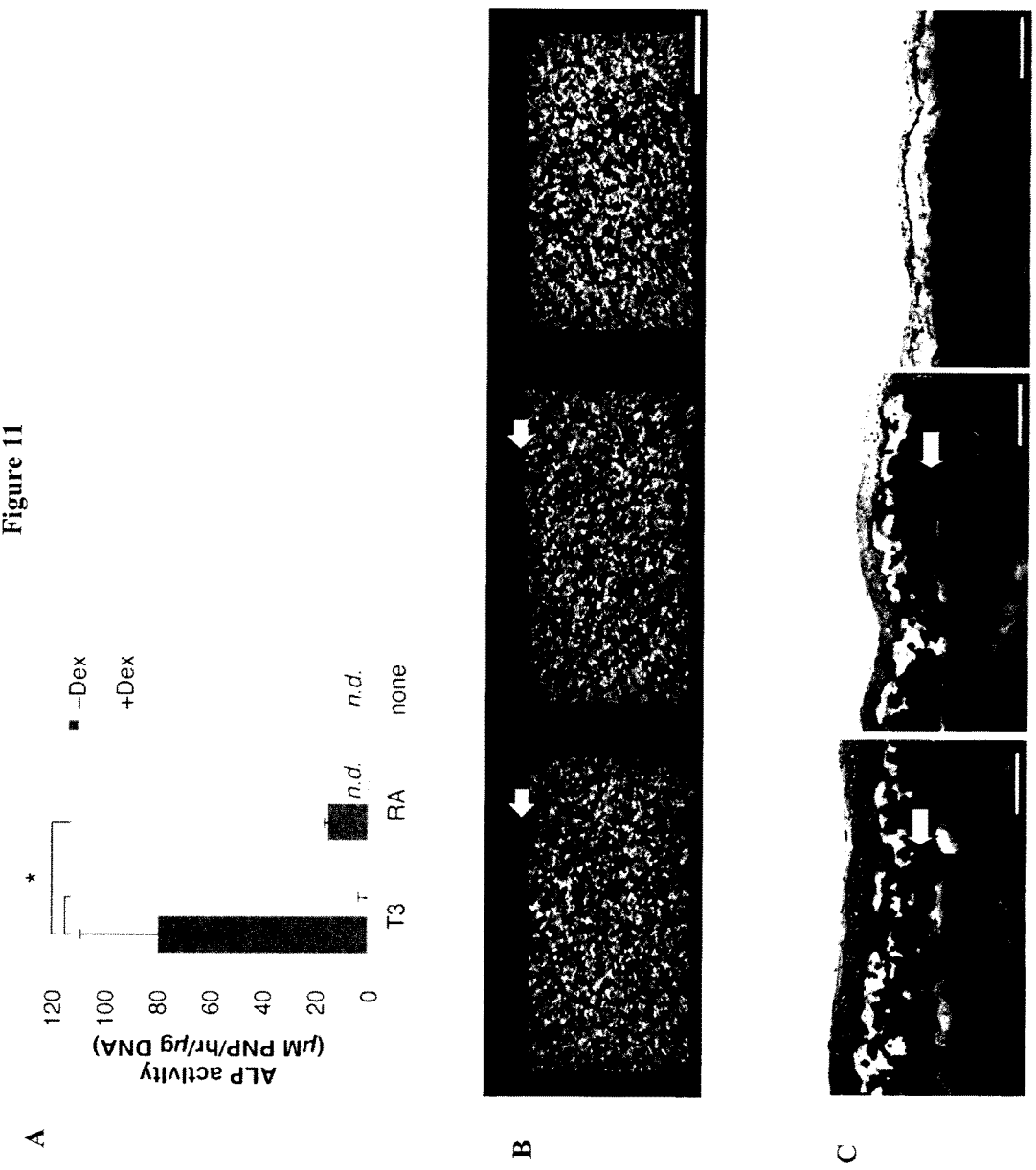
FIG. 11 shows (A) ALP activity of PDCs cultured for 7 days with 3 nM T3 or 100 nM RA in the presence or absence of dexamethasone. Mean±SD, n=3, *p<0.05. (B-C) Cross-sectional µCT tomographs (B) and histology (C) of 3-week-old constructs with decreasing numbers of initial seeded cells: $2\times10^6$ (left), $1.5\times10^6$ (middle) and $1.0\times10^6$ PDCs (right). Arrows indicate the separation between the mineralized zone and the CPP substrate. Scale bar=1 mm (B), 200 µm (C).

Optimizing the Mineralizing Culture Condition for Predifferentiated Chondrocytes To find a culture condition in which PDCs could form mineralized cartilage tissue, $1.5 \times 10^6$ PDCs were placed on the top surface of the coated CPP disks as previously described [Lee W D, et al, Tissue engineering Part C, Methods. 2011; 17:939-48], and cultured in a basal media composed of hgDMEM, 1× ITS, 100 µg/mL ascorbic acid, 50 µg/mL L-proline and 10 mM β-glycerophosphate (both Sigma-Aldrich), with or without 100 nM dexamethasone. 3 nM triiodothyronine (T3) or 100 nM retinoic acid was added to cultures. On the 7$^{th}$ day of culture, alkaline phosphatase (ALP) activity of PDCs was quantified with p-nitrophenol phosphate as previously described [Allan K S, et al, Tissue engineering. 2007; 13:167-77]. ALP activity of PDCs cultured on CPP substrates with 3 nM $T_3$ and without Dex was further characterized over the course of 14 days, and compared to those in which $T_3$ was withdrawn at the $4^{th}$ day. Mineralization of cartilaginous tissues was verified by culturing between $1.0\times10^6$ and $2.0\times10^6$ PDCs on CPP substrates for 21 days under the said culture conditions and histologically examining the cartilaginous tissues on the constructs (FIG. 11). Whole constructs were also imaged using a Skyscan 1174v2 μCT scanner (Bruker, Belgium). Scanning was performed at 50 kV and 800 μA through a 0.25 mm aluminum shield with a voxel size of 6.9 μm. After reconstruction, cross-sectional tomographs were obtained with the software provided by the manufacturer.

Tissue Culture of Multiphasic Constructs

Figure 10:
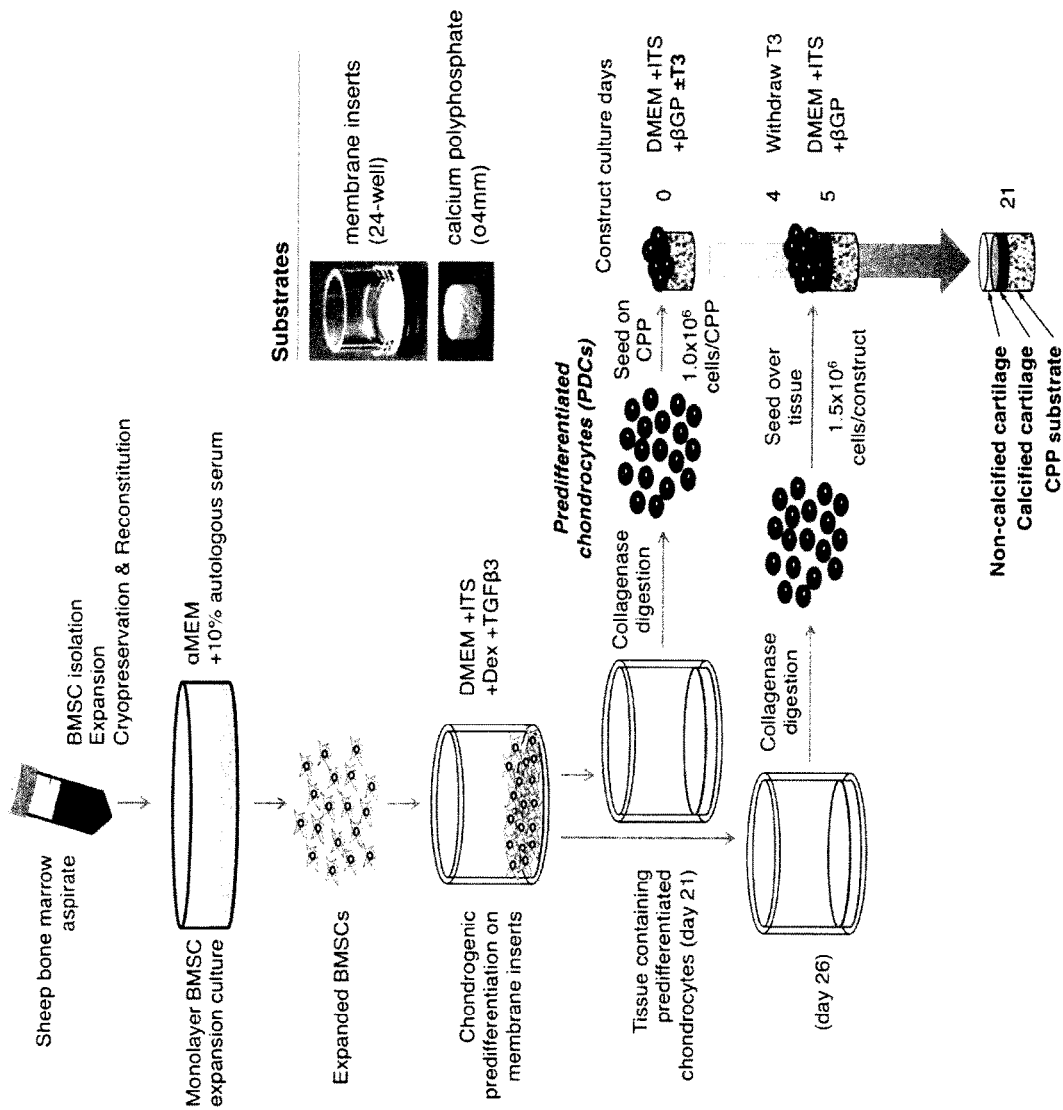
FIG. 10 shows a visual representation of the tissue culture protocol for forming the multiphasic osteochondral construct composed of non-calcified (hyaline) cartilage adherent to a zone of calcified cartilage which is integrated with the substrate (in this example, the CPP bone substitute substrate). These tissues are derived from mesenchymal stromal cells (MSC).

As shown in FIG. 10, PDCs were isolated from membrane cultures by digestion in 0.5% collagenase for 2 hours and placed on the top surface of the coated CPP disks ($1.0\times10^6$ cells per disk). Cells were cultured in a media composed of hgDMEM, 1× ITS, 100 μg/mL ascorbic acid and 10 mM β-glycerophosphate, with or without 3 nM T3. T3 was withdrawn at day 4. At day 5, additional PDCs were isolated and placed on top of the existing construct ($1.5\times10^6$ cells per construct). The multi-layered constructs were maintained in culture under the same culture conditions. Tissues were harvested at 21 days for histology, biochemical and mechanical analyses.

Histological Analysis and Immunofluorescence

Tissues were excised off the CPP substrate and fixed in 10% neutral buffered formalin for 1 hour. Then, samples were incubated in 30% (w/v) sucrose overnight at 4° C. and snap-frozen in Tissue-Tek OCT compound (Sakura Finetek, Torrance, Calif.). 6 μm cross-section cryosections were cut and mounted on silanized glass slides. Tissue mineral and proteoglycan accumulation was visualized with von Kossa and toluidine blue stain. ALP activity was visualized with azo dye (Naphthol AS-MX phosphate and Fast Blue BB salt) with an eosin counterstain. Collagen type I accumulation was visualized by treating the sections with 2.5 mg/mL trypsin and 25 mg/mL hyaluronidase and immunostaining (CalBioChem, La Jolla, Calif.). Collagen types II and X accumulations were visualized by treating the sections with 2 mg/mL pepsin and immunostaining with respective antibodies, collagen type II (Labvision, Fremont, Calif.) and type X (Sigma-Aldrich). DAPI (Life Technologies) counterstaining was applied to all immunostains.

Biochemical Analysis of Extracellular Matrix and Mineral Accumulation

Tissues were excised off the top of the CPP substrate and digested in 40 μg/mL papain for 48 hours at 65° C. as previously described [Taylor D W, et al, Tissue engineering Part A. 2010; 16:643-51]. DNA content was quantified with Hoechst 33258 dye and fluorometry (excitation at 365 nm, emission at 458 nm). The standard curve was generated using calf thymus DNA. Glycosaminoglycan content was quantified with dimethylmethylene blue dye and measuring the absorbance at 525 nm against a standard curve of chondroitin sulfate. Total collagen content was quantified using the chloramine-T/Ehrlich's reagent assay and measuring the absorbance at 561 nm. The standard curve was generated using hydroxyproline. The collagen content was calculated under the assumption that hydroxyproline comprises approximately 10% of the weight of collagen.

To measure the mineral accumulation of tissues, tissues were lyophilized, dry weights measured, and tissues were digested in 3N hydrochloric acid at 90° C. for 2 hours. The pH of samples were adjusted to 4.0 with the addition of acetate buffer. Phosphate content was determined using the heteropoly blue assay and measuring the absorbance at 620 nm. Calcium content was determined using the o-cresolphthalein complexone assay and measuring the absorbance at 570 nm [St-Pierre J-P, et al, Acta biomaterialia. 2010; 6:3302-9].

Mechanical Testing of Multiphasic Constructs

On day 21 of culture, the bulk compressive modulus of the multiphasic construct's cartilaginous tissue was determined using stress relaxation testing on the Mach-1 mechanical testing platform (Bio-Momentum, Laval, QC, Canada) with a 0.65 mm-diameter indenter as previously described. Interfacial shear strength was measured as previously described [St-Pierre J-P, et al, Acta biomaterialia. 2012; 8:1603-15]. The peak shear force before failure was calculated from the maximum stress, and the energy absorbed by the interface before failure was calculated by integrating the stress-strain curve up to the strain at which the peak shear force occurred.

Statistical Testing

Two-way analysis of variance (ANOVA) was used to analyze the effects of culture conditions and variance among donor animals. In all cases, outcome was attributed much more strongly to variation in culture condition than to variation among animals. Hence, biochemical and biomechanical data from various CPP culture conditions were evaluated using one-way ANOVA and Tukey post hoc testing. Statistical significance was assigned at $p<0.05$.

The results of the study are discussed below.

Results

Generation of Calcified Cartilage with Sheep Predifferentiated Chondrocytes at the CPP Interface To engineer a multiphasic construct that incorporates a zone of calcified cartilage at the cartilage-CPP interface using sheep PDCs, a culture condition was established in which PDCs could form mineralized cartilage tissue. Triiodothyronine (T3) [Alini M, et al, J Bone and Mineral Research. 1996; 11:105-13], retinoic acid (RA) [Iwamoto M, et al, Experimental cell research. 1993; 207:413-20], and dexamethasone [Mueller M B, and Tuan R S, Arthritis and rheumatism. 2008; 58:1377-88] were identified as potential inducers of PDC mineralization in vitro. The PDCs were cultured on CPP substrate with either T3 or RA in the presence or absence of dexamethasone for 1 week, and then the alkaline phosphate activity of the cells was quantified, which is an early indicator of chondrocyte mineralization potential [Miao D, Scutt A. J Histochem Cytochem. 2002; 50:333-40; Jiang J, et al. Osteoarthritis Cartilage. 2008; 16:70-82.]. ALP activity was maximized in sheep PDCs cultured on CPP substrates with 3 nM T3 in the absence of dexamethasone (FIG. 11A). While ALP activity was also increased in the presence of 100 μM RA in the absence of dexamethasone, prolonged culture did not yield cartilaginous tissues on CPP. Therefore, 3 nM T3 condition was selected for further study.

When $2\times10^6$ PDCs were cultured on CPP substrates for 3 weeks, the mineralized zone was found at the superior aspect of the tissue. Cells with round morphology and extracellular matrix rich in proteoglycans were observed in the intermediary zone of non-mineralized cartilage between the mineralized zone and the CPP substrate. Changing the concentration of T3 treatment did not change the location of the mineralized zone. However, when the number of initially seeded PDCs was decreased, the gap between the CPP-cartilage interface and the zone of mineralized cartilage also decreased (FIG. 11C, arrows) as the total tissue thickness decreased (FIG. 11C). At an initial seeding of $1 \times 10^6$ PDCs, the zone of mineralized cartilage formed at the substrate interface.

Short-Term Treatment of PDCs with T3 was Sufficient to Maintain ALP Activity

Figure 12:
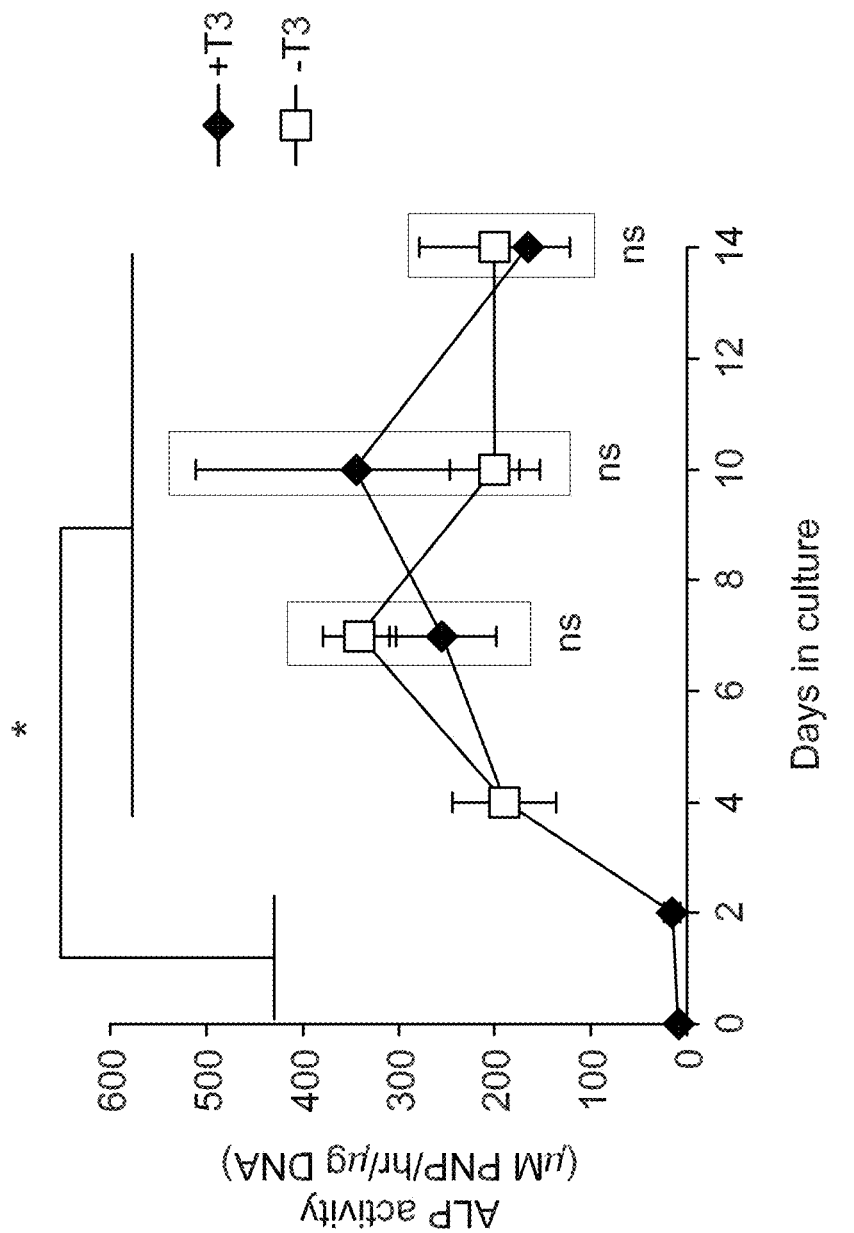
FIG. 12 illustrates that continued T3 treatment was not necessary for PDCs to maintain their capacity to mineralize its matrix. $1\times10^6$ PDCs were cultured on CPP with 3 nM T3 in the absence of dexamethasone; on day 4, T3 treatment was discontinued on day 4 (squares). n=3, mean±SD; *p<0.05; ns=not significant between individual days.

ALP activity levels of PDCs in the optimized conditions were characterized over a 2 week culture period (FIG. 12). In the presence of continuous T3 treatment, ALP activity level was significantly increased by day 4 and maintained at that level up to day 14 (p=0.334 between days 4 to 14 by 1-way ANOVA). Interestingly, when T3 was withdrawn at day 4 and subsequently cultured, ALP activity level was not significantly different by day 4 compared to those cells treated continuously with T3 (p=0.887 by 2-way ANOVA). This data demonstrated that T3 was expendable after day 4 in maintaining the ALP activity.

T3-Treated PDCs Did not Induce ALP Activity in Non-T3-Treated PDCs

Figure 13:
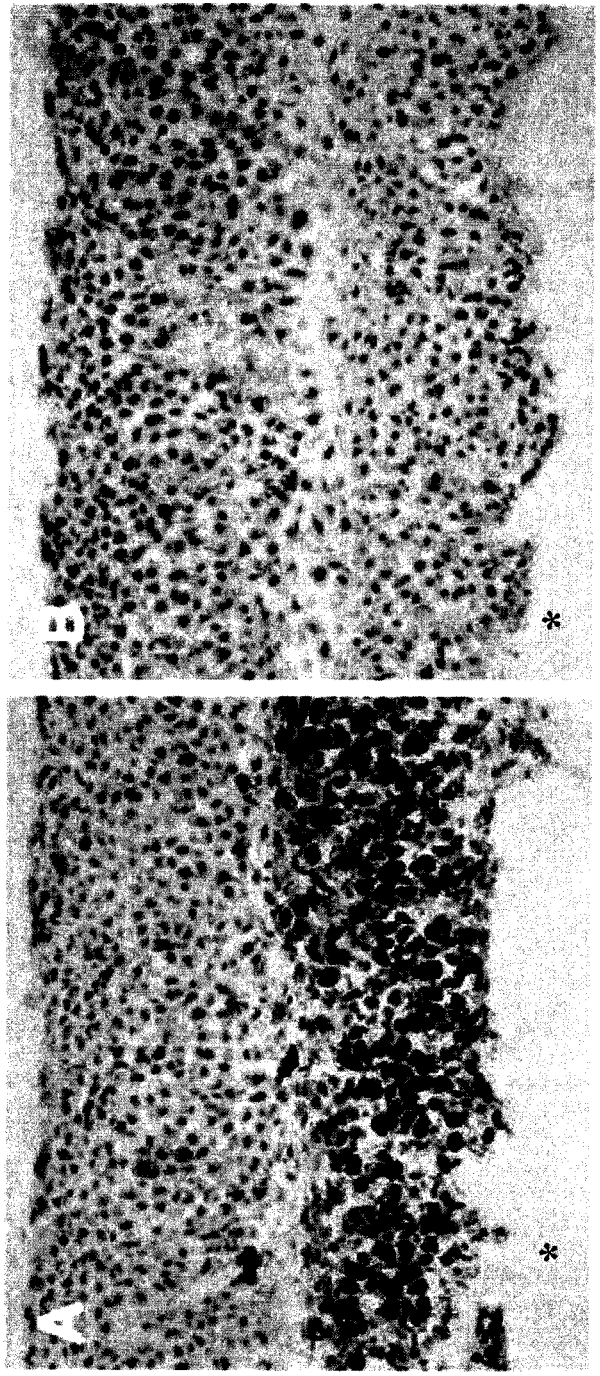
FIG. 13 shows that a layer of PDCs treated with T3 did not induce the overlaid layer of non-treated PDCs to activate ALP. $1\times10^6$ cells were cultured on CPP with (A) or without (B) 3 nM T3 for 4 days. On day 5 extra $1.5\times10^6$ cells were seeded on top without T3. Cryosections of tissues from day 10 multiphasic constructs were stained with azo dye to reveal ALP-active regions and counterstained with eosin. Asterisk denotes the location of the CPP substrate.

Based on this observation, a two-stage culture protocol was proposed (FIG. 10). To grow an interfacial zone of mineralized cartilage, $1.0 \times 10^6$ PDCs were first seeded on the CPP substrate and cultured with the T3 treatment, which was the quantity of cells that had been previously determined to be optimal for creating the mineralized cartilage at the interface (FIG. 13). Since 4 days of T3 treatment was sufficient for these cells to maintain their ALP activity (FIG. 12), T3 was withdrawn after 4 days of culture. A day later, to grow a zone of non-mineralized cartilage on top, $1.5 \times 10^6$ PDCs were seeded on top of the existing tissue and cultured with β-glycerophosphate for up to 21 days, aimed at creating a distinctively bizonal structure in the cartilage tissue on CPP. However, it was not known whether the T3-treated cells would stimulate the co-cultured, non-T3-treated cells to also mineralize, despite being cultured in conditions that did not induce a mineralizing phenotype. To address this question, tissues on the CPP substrate were harvested 5 days after the addition of the top layer (10 days of culture in total) and cryosectioned. Histological analysis demonstrated that ALP activity was present only in the bottom layer (FIG. 13A). The two-stage culture protocol without the T3 treatment of the interfacial layer was used to create a control bizonal tissue without a mineralized zone: as expected, no ALP activity was observed in either layer (FIG. 13B).

Characterization of the Multiphasic Constructs

Figure 14:
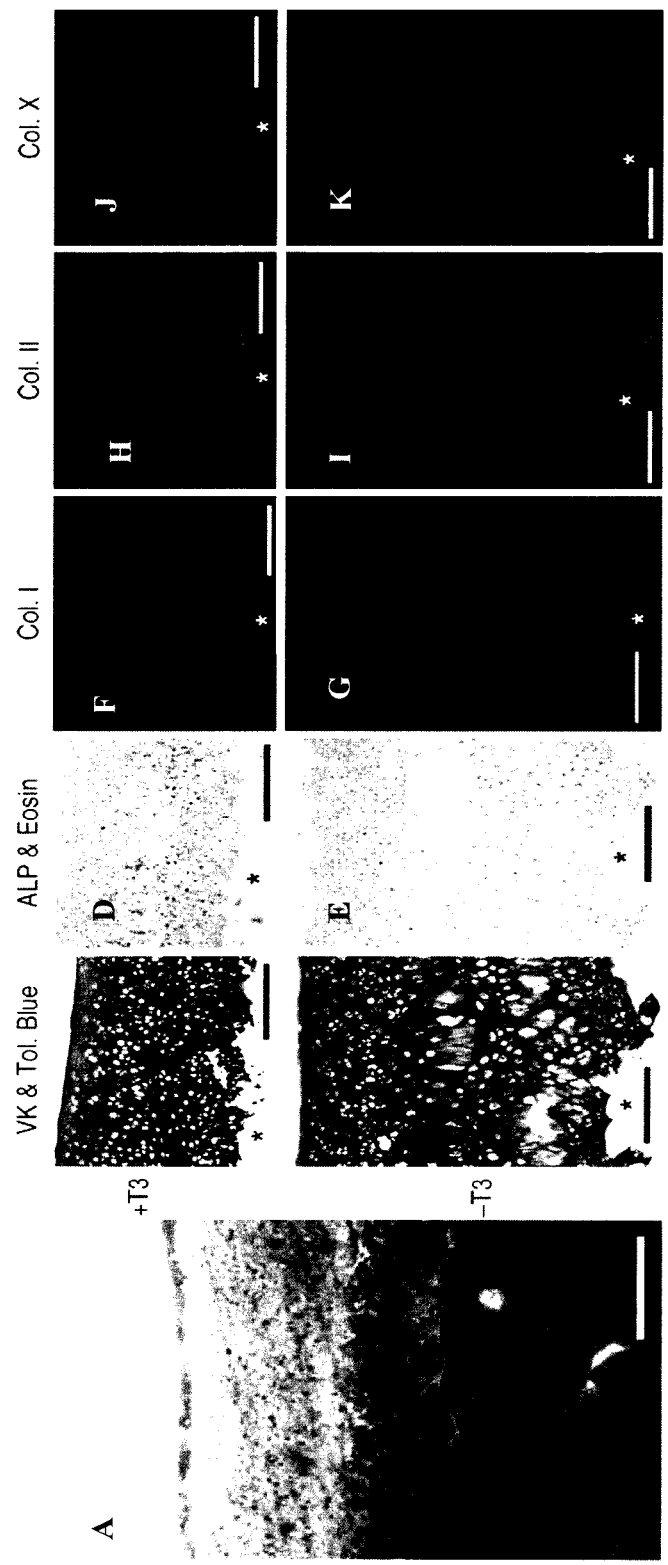
FIG. 14 shows a two-step culture protocol of PDCs on CPP substrates produced cartilage tissues with a mineralized zone at the interface. (A) Day 21 constructs with T3 treatment were infiltrated with methyl methacrylate, sectioned and stained to reveal the cartilaginous (purple), mineral (green) and CPP particles (brown). (B-K) Tissues were excised from the CPP substrate and cross-sections were examined histologically for the distribution of mineral and proteoglycan accumulation (B and C) as well as ALP activity (D and E), and with immunofluorescence for the accumulation of different types of collagen (F-K). Constructs with T3-treated interfacial layer are denoted as +T3, and those with untreated interfacial layer are denoted as −T3. Scale bars=200 µm. Representative images shown.

Constructs were grown for 21 days using the two-stage culture protocol with or without the T3 treatment of the interfacial layer and characterized using various methods. Histological examination of the whole construct revealed a zone of mineralized cartilage that formed between the zone of non-mineralized cartilage and the CPP substrate, where toluidine blue-positive cartilaginous matrix was infiltrated with fast green-positive mineral clusters (FIG. 14). The cartilage tissue on the CPP interface was distinctively bizonal in structure. Partial tissue ingrowth through the CPP substrate was also observed, with the mineral clusters directly in contact with the CPP particles.

Figure 15A:
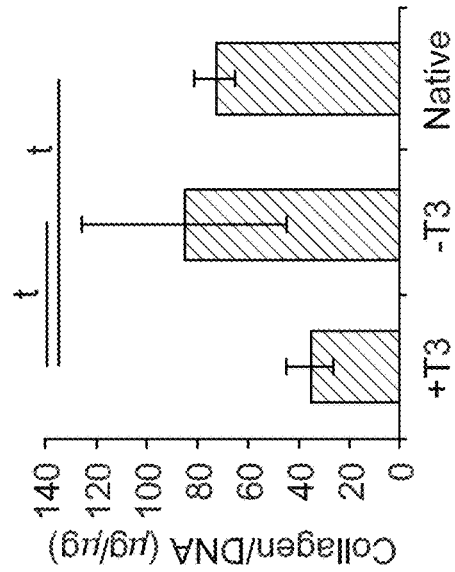
FIG. 15 shows the accumulation of extracellular matrix in tissues on $T_3$-treated (+T3) constructs was less compared to those on untreated (−T3) constructs, but comparable to native articular cartilage. Accumulated proteoglycans (A) and total collagens (B) were quantified in the digested samples and normalized by their DNA content. Accumulation of mineral in tissue was represented by the calcium and phosphate contents, normalized by the tissue dry weight (C). "Native" denotes data from sheep cartilage explants of femoral condyles, reproduced from Lee W D, et al [Tissue engineering Part C, Methods. 2011; 17:939-48]. In (A), difference between +T3 and Native is not statistically significant. n=6, mean±SD. †p<0.05, *p<0.01.
Figure 15B:
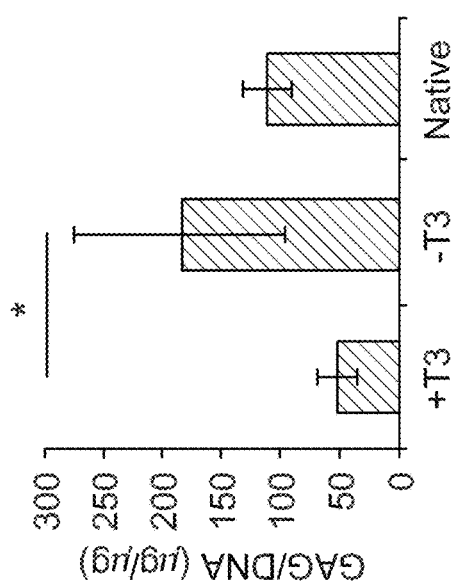
Figure 15C:
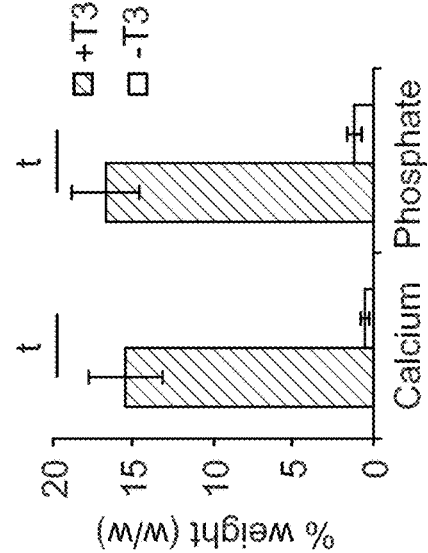
Figure 16B:
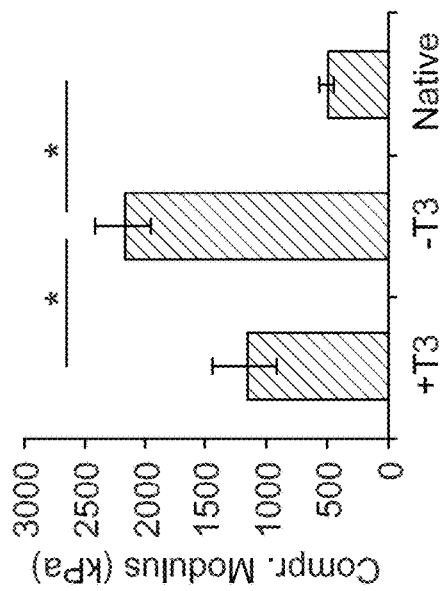
FIG. 16 shows $T_3$-treated constructs (+T3) exhibited comparable compressive strength as native osteochondral constructs and stronger shear strength than untreated constructs (−T3). (A) Tissue thickness was measured directly from the outside edge using a caliper under a dissection microscope. (B) Compressive modulus was measured by stress relaxation test with a 0.65 mm-diameter indenter situated at the centre of the constructs and explants. (C,D) A shear load to the cartilage-CPP interface was applied until failure at a displacement rate of 1 mm/min. In (B), difference between +T3 and Native is not statistically significant. n=9 for constructs and 6 for explants. Mean±SD (A), mean±SEM (B-D). †p<0.05, *p<0.01.
Figure 16D:
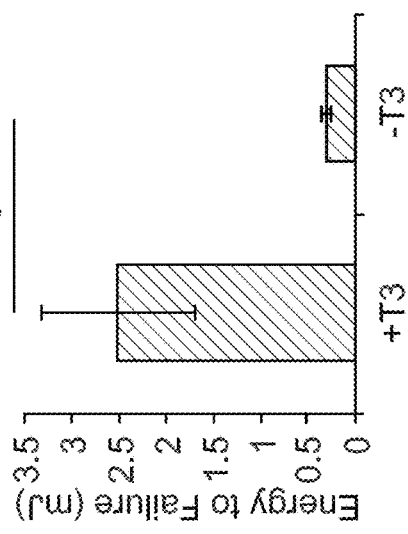
Figure 16A:
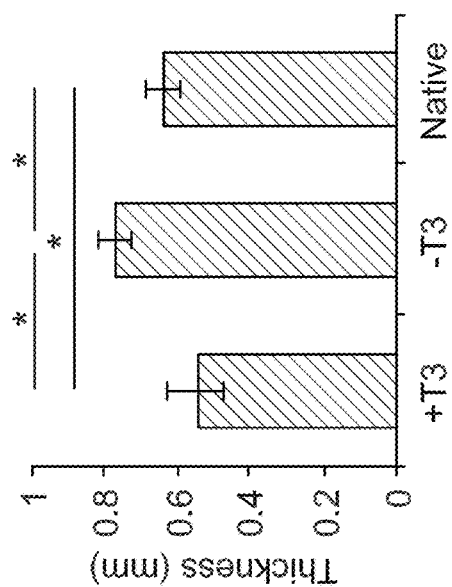
Figure 16C:
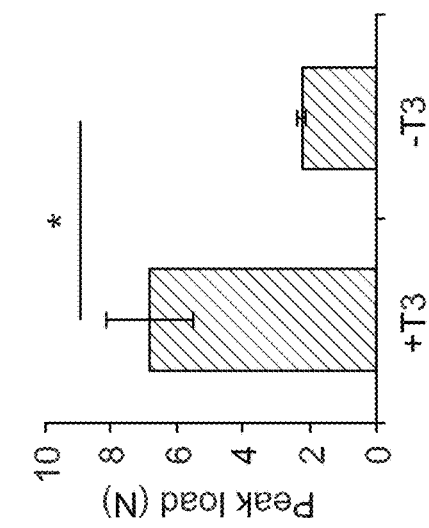

Histological examination of cartilage tissue on the constructs showed bizonal tissue organization with a zone of articular cartilage-like tissue rich in type II collagen and proteoglycan (FIG. 14). Type X collagen was localized to this zone that also had ALP activity (FIG. 14). No type I collagen was detected (FIG. 14D). In contrast, control constructs not exposed to T3 did not show a bizonal composition as there was no zone of calcified cartilage, and had an uneven distribution of extracellular matrix (FIG. 14). Tissues on T3-treated constructs accumulated less proteoglycans (FIG. 15A) and collagens (FIG. 15B) compared to those on untreated constructs, but showed comparable amounts as native sheep cartilage. As expected, tissues on T3-treated constructs accumulated calcium and phosphate, while those on untreated constructs did not (FIG. 15C).

Mechanical Properties of the Multiphasic Constructs

T3-treated and non-treated constructs were characterized for their mechanical properties using the stress relaxation test for measuring compressive modulus as previously described, and interfacial shear stress test by measuring the resistance to shear stress (FIG. 16). Tissues on T3-treated constructs had a comparable bulk compressive modulus to osteochondral explants obtained from native sheep femoral condyles (p=0.15). T3-treated constructs' interface exhibited a higher peak shear force and the energy prior to failure than the non-treated constructs, demonstrating that mineralizing the tissue interface enhanced the interfacial shear strength. Gross examination of shear sites showed that all failures occurred at the cartilage-CPP interface.

The results of the study are discussed below. In this study, the first successful generation of an osteochondral construct is reported comprised of BMSC-derived cartilage tissue and porous CPP substrate, interfaced with a zone of calcified cartilage, which was created without using any exogenous scaffolds. The two-stage culture protocol enabled the selective stimulation of predifferentiated chondrocytes to form calcified cartilage only at the interface. This organization in the cartilaginous tissue on CPP was confirmed by the accumulation of collagen type X and mineral in addition to collagen type II and proteoglycans only at the part of the tissue that was treated with mineralization-inducing T3, which faced the CPP substrate. The interfacial shear strength of constructs with the calcified cartilaginous interface was increased significantly compared to those without it, functionally validating its intended effect.

The development of this two-stage culture protocol was prompted by the observation that BMSC-derived predifferentiated chondrocytes (PDCs) formed calcified cartilage at the tissue's superficial aspect with pro-mineralizing stimulus. Given that T3 was delivered to the tissue through culture media, and that the location of calcified cartilage did not change with tissue thickness, this effect was likely due to T3's diffusion into the tissue. Without scaffolds, selective delivery of T3 to the interface was difficult to achieve with media alone. On the other hand, by seeding limited numbers of cells to the CPP and generating thin cartilaginous tissue, mineralization took place juxtaposed to the CPP substrate. This was used as an interface to the subsequently cultured, non-mineralized cartilage grown with the same cell type. The presence of collagen types II, X and proteoglycans in the calcified interface, as well as the absence of collagen type I, is an important point of distinction in this study. This demonstrates that the interface was cartilaginous, not bony, successfully recapitulating the characteristics of the healthy articular cartilage-subchondral bone interface in vivo.

Histology showed that the layer of non-mineralized cartilage successfully fused to the T3-treated tissue underneath, but fissures were observed if the intended interfacial tissue was not treated with T3. Total thickness of cartilage tissues on these constructs appeared increased and the extracellular matrix was unevenly distributed. A possible explanation may be attributed to the growth of the interfacial layer: BMSC-derived chondrocytes share many characteristics with proliferating cartilage [Dickhut A, et al, Journal of cellular physiology. 2009; 219:219-26] that grows appositionally. In development, Indian hedgehog, FGF and BMP signaling pathways regulate this appositional growth; however, in lieu of this regulation, the interfacial layer may also expand laterally. The presence of tubing around the constructs prevented lateral expansion by confinement, which could have resulted in lateral mechanical stress and caused the tissue to buckle and shear. This was not the case for T3-stimulated interfacial layer, however, whose behaviour may resemble more of terminal hypertrophic chondrocytes, as evidenced by their mineralized matrix.

Although the multiphasic construct possesses inferior interfacial shear strength compared to articular cartilage, it still represented a four-fold improvement over the non-mineralized control, and sheep gait studies suggest that this improvement is adequate for preventing delamination.

An important feature of the protocol was that no xenogeneic material was employed in generating the multiphasic constructs. The culture media used to isolate and expand BMSCs are commonly supplemented with fetal bovine serum (FBS). However, BMSCs may internalize and express FBS antigens, and it has been demonstrated that substitution of FBS with autologous serum can minimize its downstream immunogenicity [Horwitz E M, et al, Proceedings of the National Academy of Sciences of the United States of America. 2002; 99:8932-7; Spees J L, et al, Molecular therapy: the journal of the American Society of Gene Therapy. 2004; 9:747-56]. In addition, while undifferentiated BMSCs have immunomodulatory properties that enabled its application in treating graft-versus-host disease [Francois M, and Galipeau J., Journal of cellular physiology. 2012], BMSCs that have undergone chondrogenesis lose this property and become immunogenic [Chen X, et al, Stem cells (Dayton, Ohio). 2007; 25:364-70]. To minimize the risk of rejection, the culture media used to isolate and expand sheep BMSCs in this study were supplemented with autologous sheep serum. Therefore, the strategy is ready to be directly applied to generating constructs for in vivo use. However, use of autologous serum can also contribute to the variability between animals compared to using a single, screened lot of FBS.

Using the expansion technique in this study, $3\times10^8$ BMSCs were successfully obtained from a single sheep bone marrow aspirate within 2 passages. CPP particles can be arranged using a solid freeform fabrication process to generate substrates of arbitrary shapes and sizes [Shanjani Y, et all, J Biomed Mater Res B Appl Biomater. 2010; 93:510-9]. Solid freeform fabricated CPP exhibited the same degree of osseointegration after implantation as those produced conventionally [Shanjani Y, et al, J Biomed Mater Res B Appl Biomater. 2013; 101:972-80].

The present disclosure is not to be limited in scope by the specific embodiments described herein, since such embodiments are intended as but single illustrations of one aspect of the disclosure and any functionally equivalent embodiments are within the scope. Indeed, various modifications in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methodologies, reagents, etc. which are reported therein which might be used in connection with the disclosure. Nothing herein is to be construed as an admission that the present disclosure is not entitled to antedate such disclosure by virtue of prior invention.

What is claimed is:

1. A method for preparing an integrated intervertebral disc implant comprising
   (a) preparing a first construct by culturing nucleus pulposus (NP) cells or precursors on a substrate to form a continuous layer of NP tissue directly or indirectly on and integrated with the substrate;
   (b) preparing a second construct by culturing annulus fibrosus (AF) cells or precursors thereof on a scaffold to form two or more continuous layers of AF tissue-scaffold, wherein the layers are adherent to each other to form a single tissue;
   (c) combining the first construct and second construct so that the second construct surrounds the first construct and the NP tissue and AF tissue are adjacent; and
   (d) culturing the combined first construct and second construct to prepare the integrated intervertebral disc implant;
   further comprising prior to (a), forming a layer of cartilaginous tissue on the substrate by seeding isolated chondrocytes or chondrocytes obtained from precursor cells grown under chondro-inducing conditions on the substrate; and culturing the chondrocytes in the presence of a mineralizing agent under suitable conditions to generate a calcified cartilage tissue on the substrate characterized by accumulation of collagen type X, mineral, collagen type II and proteoglycans.

2. The method of claim 1, further comprising culturing additional isolated chondrocytes or stem cell precursors or precursor derived chondrocytes on the calcified cartilage tissue to generate a bizonal cartilage tissue comprising a continuous layer of cartilage tissue engineered on the substrate interfaced with a zone of calcified cartilage tissue.

3. A method for preparing an integrated intervertebral disc implant comprising
   (a) preparing a first construct by culturing nucleus pulposus (NP) cells or precursors on a substrate to form a continuous layer of NP tissue directly or indirectly on and integrated with the substrate;
   (b) preparing a second construct by culturing annulus fibrosus (AF) cells or precursors thereof on a scaffold to form two or more continuous layers of AF tissue-scaffold, wherein the layers are adherent to each other to form a single tissue;
   (c) combining the first construct and second construct so that the second construct surrounds the first construct and the NP tissue and AF tissue are adjacent; and
   (d) culturing the combined first construct and second construct to prepare the integrated intervertebral disc implant,
   wherein (a) further comprises preparing a first construct by:
      i. seeding isolated chondrocytes or chondrocytes obtained from precursor cells grown under chondro-inducing conditions on a substrate;
      ii. culturing the chondrocytes in the presence of a mineralizing agent under suitable conditions to generate a calcified cartilage tissue on the substrate characterized by accumulation of collagen type X, mineral, collagen type II and proteoglycans; and
      iii. culturing NP cells or precursors on the cartilage/substrate produced in ii. to form a continuous layer of NP tissue on and adherent to the cartilaginous layer which is on and integrated with the substrate.

4. The method of claim 3, further comprising in (a) culturing isolated chondrocytes on the engineered calcified cartilage tissue to generate a bizonal cartilage tissue comprising a continuous layer of cartilage tissue engineered on the substrate interfaced with a zone of calcified cartilage tissue after (a)ii. and before (a)iii.

5. The method of claim 1, wherein the substrate is bone or an engineered biomaterial.

6. The method of claim 5, wherein the engineered biomaterial is a bone substitute.

7. The method of claim 6, wherein the bone substitute is CPP.

8. The method of claim 1, wherein the scaffold is a polymeric scaffold or a synthetic polymeric scaffold.

9. The method of claim 1, wherein the scaffold comprises one or more of:
(i) polyurethane fibres;
(ii) polycarbonate urethane (PU) fibres; and
(iii) low molecular weight polymer additives containing hydroxyl/carboxylic acid groups that enhance cell and/or protein interactions with the scaffold.

10. The method of claim 3, wherein the substrate is bone or an engineered biomaterial.

11. The method of claim 10, wherein the engineered biomaterial is a bone substitute.

12. The method of claim 11, wherein the bone substitute is CPP.

13. The method of claim 3, wherein the scaffold is a polymeric scaffold or a synthetic polymeric scaffold.

14. The method of claim 3, wherein the scaffold comprises one or more of:
(i) polyurethane fibres;
(ii) polycarbonate urethane (PU) fibres; and
(iii) low molecular weight polymer additives containing hydroxyl/carboxylic acid groups that enhance cell and/or protein interactions with the scaffold.

* * * * *